(12) United States Patent
Cohen et al.

(10) Patent No.: US 12,304,931 B2
(45) Date of Patent: *May 20, 2025

(54) MENTSH ANALOGS AS THERAPEUTICS FOR DIABETES, OBESITY, AND THEIR ASSOCIATED DISEASES AND COMPLICATIONS

(71) Applicant: University of Southern California, Los Angeles, CA (US)

(72) Inventors: Pinchas Cohen, Los Angeles, CA (US); Kelvin Yen, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/363,178

(22) Filed: Aug. 1, 2023

(65) Prior Publication Data

US 2024/0018199 A1   Jan. 18, 2024

Related U.S. Application Data

(63) Continuation of application No. 17/394,282, filed on Aug. 4, 2021, now Pat. No. 11,760,783, which is a continuation of application No. 16/311,599, filed as application No. PCT/US2017/039139 on Jun. 23, 2017, now Pat. No. 11,124,551.

(60) Provisional application No. 62/354,573, filed on Jun. 24, 2016.

(51) Int. Cl.
| | |
|---|---|
| A61K 38/00 | (2006.01) |
| A61P 3/04 | (2006.01) |
| A61P 3/10 | (2006.01) |
| C07K 7/08 | (2006.01) |
| C07K 14/435 | (2006.01) |
| C07K 14/47 | (2006.01) |
| G01N 33/68 | (2006.01) |

(52) U.S. Cl.
CPC ............. *C07K 14/47* (2013.01); *A61K 38/00* (2013.01); *A61P 3/04* (2018.01); *A61P 3/10* (2018.01); *C07K 7/08* (2013.01); *C07K 14/435* (2013.01); *G01N 33/6893* (2013.01); *G01N 2800/04* (2013.01); *G01N 2800/042* (2013.01); *G01N 2800/044* (2013.01); *G01N 2800/347* (2013.01)

(58) Field of Classification Search
CPC ... A61K 38/00; A61P 3/04; A61P 3/10; C07K 14/435; C07K 14/47; C07K 7/08
See application file for complete search history.

(56) References Cited

U.S. PATENT DOCUMENTS

| | | |
|---|---|---|
| 11,124,551 B2 | 9/2021 | Cohen et al. |
| 2003/0109690 A1 | 6/2003 | Ruben et al. |
| 2004/0101874 A1 | 5/2004 | Ghosh et al. |
| 2010/0267041 A1 | 10/2010 | Shuber et al. |
| 2011/0039771 A1 | 2/2011 | Cohen et al. |
| 2011/0237461 A1 | 9/2011 | Chinnaiyan et al. |
| 2014/0213527 A1 | 7/2014 | Cohen et al. |
| 2014/0296139 A1 | 10/2014 | Cohen et al. |
| 2019/0194275 A1 | 6/2019 | Cohen et al. |
| 2021/0371479 A1 | 12/2021 | Cohen et al. |

FOREIGN PATENT DOCUMENTS

| | | |
|---|---|---|
| AU | 2017280348 A2 | 1/2019 |
| CA | 3026458 A1 | 12/2017 |
| CN | 105229023 A | 1/2016 |
| CN | 109414472 A1 | 3/2019 |
| EP | 3474877 A1 | 5/2019 |
| JP | 2019524666 A1 | 9/2019 |
| KR | 20190020693 A | 3/2019 |
| MX | 2018015869 A1 | 8/2019 |
| WO | 2011/116209 A2 | 9/2011 |
| WO | 2017/223533 A1 | 12/2017 |

OTHER PUBLICATIONS

Q9UJ68 from UniProtKB, Integrated into UniProtKB/Swiss-Prot on Jan. 11, 2001. pp. 1-15. (Year: 2001).*
International Search Report and Written Opinion for PCT/US2017/039139 dated Sep. 21, 2017, 12 pages.
International Preliminary Report on Patentability dated Dec. 25, 2018, 8 pages.
EP 17816353.1 European Search Report dated Oct. 25, 2019, 9 pages.
Armstrong et al., Mitochondrial Medicine: Pharmacological Targeting of Mitochondria in Disease, British Journal of Pharmacology, 2007, vol. 151(8), pp. 1154-1165.
Diabetes from https://www.cdc.gov/diabetes/library/features/hispanic-diabetes.html on Feb. 2, 2020, pp. 1-3.

(Continued)

*Primary Examiner* — Julie Ha
(74) *Attorney, Agent, or Firm* — Nixon Peabody LLP

(57) ABSTRACT

Described herein is a novel, mitochondrial encoded, open reading frame, that leads to the production of a new mitochondrial peptide. Residing within the ND-Two subunit, a specific small nucleotide polymorphism disrupts expression of this mitochondrial peptide, and is correlated with an increase in obesity and diabetes, particularly in certain ethnic populations. In vitro administration of the peptide increases insulin secretion, decreases fat accumulation and improves glucose uptake in muscle cell. Antibodies generated against the peptide can be used for detecting peptide deficiency, in addition to SNP detection, supporting diagnostic approaches. In vivo studies further revealed that administration of the peptide improves glucose tolerance, thereby providing a new therapeutic avenue for a novel diabetes therapy and decreases bodyweight, thus serving as a novel obesity therapy. Generation of synthetic analogs further enhance or abrogated activity relative to the natural peptide.

10 Claims, 24 Drawing Sheets

Specification includes a Sequence Listing.

(56) References Cited

OTHER PUBLICATIONS

Mitochondrial Peptide Methionine Sulfoxide Reductase (MSRA_HUMAN), UniProtKB-Q9UJ68, pp. 14-15, 2001.
Yampolsky et al., The Exchangeability of Amino Acids in Proteins, Genetics, 2005, vol. 170, pp. 1459-1472.
CN 109414472 A Office Action dated Nov. 26, 2021, 10 pages.
First OA for MX2018015869 dated Mar. 9, 2022.
Mero, Leucine Supplementation and Intensive Training, Sports Med. 1999, 27(6)347-358.

* cited by examiner

MENTSH ANALOGS AS THERAPEUTICS FOR DIABETES, OBESITY, AND THEIR ASSOCIATED DISEASES AND COMPLICATIONS

CROSS-REFERENCE TO RELATED APPLICATIONS

This application is a continuation of U.S. application Ser. No. 17/394,282, filed Aug. 4, 2021, which is a continuation of U.S. application Ser. No. 16/311,599, filed Dec. 19, 2018, now issued as U.S. Pat. No. 11,124,551, which is a National Phase of International Application No. PCT/US2017/039139, filed Jun. 23, 2017, which designated the U.S. and that International Application was published under PCT Article 21(2) in English, which claims priority under 35 U.S.C. § 119(e) to U.S. Provisional Application No. 62/354,573, filed Jun. 24, 2016, the contents of which are herein incorporated by reference in their entirety.

STATEMENT REGARDING FEDERALLY SPONSORED RESEARCH OR DEVELOPMENT

This invention was made with government support under grant Nos. GM090311 and AG034906 awarded by the National Institutes of Health. The government has certain rights in the invention.

REFERENCE TO SEQUENCE LISTING

This application contains a Sequence Listing submitted as a computer readable form named "SequenceListing-065715-000078USC2.xml", having a size in bytes of 121,847 bytes, and created on Jul. 24, 2023. The information contained in this computer readable form is hereby incorporated by reference in its entirety.

FIELD OF THE INVENTION

Described herein are methods and compositions related to mitochondrial peptides for use in treating metabolic related disease and compositions, such as diabetes, obesity, and dyslipidemia.

BACKGROUND

Diabetes mellitus is associated with continuous and pathologically elevated blood glucose concentration. According to the American Diabetes Association, the disease causes thousands of deaths every year and costs more than $20 billion annually. It is predicted that the number of diabetic people will increase to 440 million by 2030, and treatment options for these people are limited and often insufficient.

Medications used to treat diabetes do so by lowering blood sugar levels. There are a number of different classes of anti-diabetic medications. Insulin, sulfonylureas, and glucagon-like peptide-1 (GLP-1) receptor agonists are major classes of diabetes medicines prescribed today in the United States. Insulin is prescribed for both Type 1 and Type 2 diabetes, while sulfonylureas and GLP-1 agonists are usually prescribed for Type 2 diabetics. While sulfonylureas and GLP-1 agonists can stimulate natural insulin secretion and reduce insulin resistance, these compounds do not replace the function of insulin in metabolism. Many anti-diabetic agents also have an undesired side effect of increasing body weight. Increased body weight in patients with diabetes mellitus results in deleterious effects due to accentuation of the metabolic and endocrine dysregulation. This actually can be a risk factor for progressive worsening of diabetes. There is a great need in the art for therapeutic interventions for diabetes with persistent effects and without undesirable side effects.

Mitochondrial peptides represent a novel class of molecules for treatment of human diseases. It is now well-established that mitochondria are key actors in generating energy and regulating cell death. Mitochondria communicate back to the cell via retrograde signals that are encoded in the nuclear genome, or are secondary products of mitochondrial metabolism. More recently, mitochondrial-derived peptides that are encoded by the mitochondrial genome have been identified as important actors in these regulatory processes. It is widely believed that mitochondrial-derived retrograde signal peptides will aid in the identification of genes and peptides with therapeutic and diagnostic to treat human diseases.

Described herein are methods and compositions for treatment using novel mitochondrial peptides. Identified via genome wide scanning, SNP mutations associated with the novel mitochondrial peptide are associated with obesity and diabetes. Administration of the peptide, increases insulin secretion, decreases fat accumulation, and improves glucose uptake in muscle cell. Importantly, administration of the mitochondrial peptide improves glucose tolerance of mice fed a high-fat/"western" diet, thus serving as a novel diabetes therapy and decreases bodyweight in mice fed a high-fat diet, thus serving as a novel obesity therapy.

SUMMARY OF THE INVENTION

Described herein is a composition including a mitochondrial peptide. In various embodiments, the mitochondrial peptide includes the amino acid sequence set forth in SEQ ID NO:97. In various embodiments, the mitochondrial peptide includes an amino acid sequence with about 25%, 30%, 35%, 40%, 45%, 50%, 55%, 60%, 65%, 70%, 75%, 80%, 85% or more percentage identity to SEQ ID NO:97. In various embodiments, the mitochondrial peptide is 14, 16, 17, 18, 19, 20, 21, 22, 23, or 24 amino acids in length. In various embodiments, the mitochondrial peptide possesses a post-translational or artificial modification. In various embodiments, the artificial modification includes pegylation, fatty-acid conjugation, polypeptide extension, IgG-Fc, CPT, HSA, ELP, transferrin, or albumin modification.

Further described herein is a method of treating a disease and/or condition comprising selecting a subject in need of treatment and administering a quantity of a mitochondrial peptide to a subject in need of treatment, wherein the mitochondrial peptide is capable of treating the disease and/or condition. In various embodiments, the mitochondrial peptide includes the amino acid sequence set forth in SEQ ID NO:97. In various embodiments, the mitochondrial peptide includes an amino acid sequence with about 25%, 30%, 35%, 40%, 45%, 50%, 55%, 60%, 65%, 70%, 75%, 80%, 85% or more percentage identity to SEQ ID NO:97. In various embodiments, the mitochondrial peptide is 14, 15, 16, 17, 18, 19, 20, 21, 22, 23, or 24 amino acids in length. In various embodiments, the disease and/or condition includes a disease and/or condition characterized by reduced blood insulin level and/or reduced number or function of pancreatic beta islet cells. In various embodiments, the disease and/or condition includes type 1 and type 2 diabetes, gestational diabetes, pre-diabetes, insulin resistance, metabolic syndrome, impaired glucose tolerance and dyslipidemia.

In various embodiments, the disease and/or condition further includes retinopathy, neuropathy, renal diseases. In various embodiments, the disease and/or condition includes obesity or overweight. In various embodiments, the subject is Hispanic. In various embodiments, the subject is a carrier of the SNP Rs28357981. In various embodiments, the subject expresses low amounts of SEQ ID NO:97 measured in biological samples relative to a healthy normal subject without diabetes and/or obesity.

Further described herein is a method of diagnosing an individual for a disease and/or condition including selecting a subject and detecting the presence, absence, or expression level of one or more biomarkers; and diagnosing the subject for a disease and/or condition, based on the presence, absence, or expression level of the one or more biomarkers. In various embodiments, the one or more biomarkers includes a peptide of the sequence set forth in SEQ ID NO:97. In various embodiments, detecting the presence, absence, or expression level includes an immunoassay. In various embodiments, the one or more biomarkers includes the SNP Rs28357981.

BRIEF DESCRIPTION OF THE FIGURES

Exemplary embodiments are illustrated in referenced figures. It is intended that the embodiments and figures disclosed herein are to be considered illustrative rather than restrictive.

DETAILED DESCRIPTION OF THE INVENTION

Figure 1:
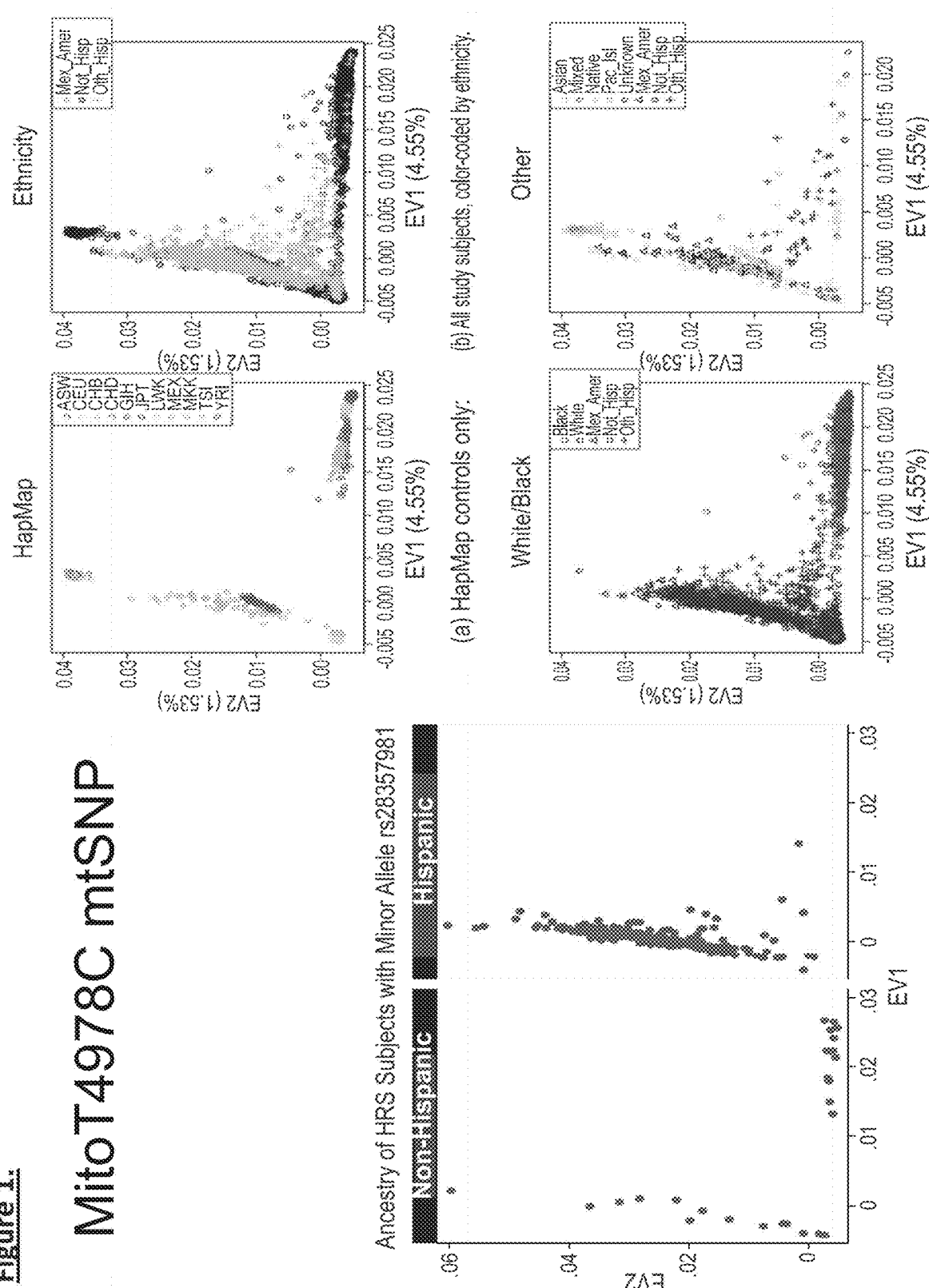
FIG. 1. GWAS for 9,825 HRS participants to examine the association between mitochondrial variants and glycosylated hemoglobin. The GWAS was run for 68 mitochondrial SNPs with minor allele frequencies>0.01. Models were adjusted for age and population stratification (the first 4 Eigen-values). One SNP (MitoT4978C) was found to be significantly associated with HbA1c after adjusting for multiple-testing (P=4.9E-04, Bonferroni P=0.03). Results showed that the SNP is associated with a 38% increase in the risk of diabetes. The SNP is far more common in participants who self-identify as Hispanic (MAFHispanic=18.65 vs. MAFNon-Hispanic=0.27).

All references cited herein are incorporated by reference in their entirety as though fully set forth. Unless defined otherwise, technical and scientific terms used herein have the same meaning as commonly understood by one of ordinary skill in the art to which this invention belongs.

Allen et al., Remington: The Science and Practice of Pharmacy 22$^{nd}$ ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3 rd ed., revised ed., J. Wiley & Sons (New York, NY 2006); Smith, March's Advanced Organic Chemistry Reactions, Mechanisms and Structure 7$^{th}$ ed., J. Wiley & Sons (New York, NY 2013); Singleton, Dictionary of DNA and Genome Technology 3$^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, NY 2012), provide one skilled in the art with a general guide to many of the terms used in the present application. For references on how to prepare antibodies, see Greenfield, Antibodies A Laboratory Manual 2$^{nd}$ed., Cold Spring Harbor Press (Cold Spring Harbor NY, 2013); Köhler and Milstein, Derivation of specific antibody-producing tissue culture and tumor lines by cell fusion, Eur. J. Immunol. 1976 Jul., 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Indeed, the present invention is in no way limited to the methods described herein. For purposes of the present invention, the following terms are defined below.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Modulation" or "modulates" or "modulating" as used herein refers to upregulation (i.e., activation or stimulation), down regulation (i.e., inhibition or suppression) of a response or the two in combination or apart.

"Pharmaceutically acceptable carriers" as used herein refer to conventional pharmaceutically acceptable carriers useful in this invention.

"Promote" and/or "promoting" as used herein refer to an augmentation in a particular behavior of a cell or organism.

"Subject" as used herein includes all animals, including mammals and other animals, including, but not limited to, companion animals, farm animals and zoo animals. The term "animal" can include any living multi-cellular vertebrate organisms, a category that includes, for example, a mammal, a bird, a simian, a dog, a cat, a horse, a cow, a rodent, and the like. Likewise, the term "mammal" includes both human and non-human mammals.

"Therapeutically effective amount" as used herein refers to the quantity of a specified composition, or active agent in the composition, sufficient to achieve a desired effect in a subject being treated. A therapeutically effective amount may vary depending upon a variety of factors, including but not limited to the physiological condition of the subject (including age, sex, disease type and stage, general physical condition, responsiveness to a given dosage, desired clinical effect) and the route of administration. One skilled in the clinical and pharmacological arts will be able to determine a therapeutically effective amount through routine experimentation.

"Treat," "treating" and "treatment" as used herein refer to both therapeutic treatment and prophylactic or preventative measures, wherein the object is to prevent or slow down (lessen) the targeted condition, disease or disorder (collectively "ailment") even if the treatment is ultimately unsuccessful. Those in need of treatment may include those already with the ailment as well as those prone to have the ailment or those in whom the ailment is to be prevented.

As described, mitochondria are responsible for crucial cellular activities including energy production, regulation of programmed cell death (apoptosis), and biosynthetic precursor production, among others. Until recently, little was understood about how mitochondria transmit information to the host cell. Shedding light on these processes, a novel class of communication conveyed by the mitochondrion to regulate cellular processes and cell fate has been described. It is now better understood that that mitochondria are no longer mere 'end-function' organelles, but possess vital roles in cellular regulatory processes. Specifically, mitochondria communicate back to the cell via retrograde signals that are encoded in the nuclear genome, are secondary products of mitochondrial metabolism, or, as more recently discovered, encoded by the mitochondrial genome. As an example of the latter, humanin, the first small peptide of a putative set of mitochondrial-derived peptides, has been reported as exhibiting strong cytoprotective actions against various stress and disease models. Exploiting the features and capabilities of this novel class of molecules allows for new diagnostic and therapeutic avenues.

Described herein is a novel, mitochondrial encoded open reading frame that leads to the production of a new polypeptide called MENTSH (Mitochondrial-derived peptide Encoded in the ND-Two Subunit of Humans) MENTSH and analogs thereof represent a new class of mitochondrial-derived peptides that will aid in the identification of genes and peptides with therapeutic and diagnostic potential in treating human diseases, including diabetes and obesity. Mitochondrially encoded NADH dehydrogenase 2 is protein that in humans is encoded by the mitochondrial gene MT-ND2 gene. The ND2 protein is a subunit of NADH dehydrogenase (ubiquinone), and is located in the mitochondrial inner membrane. As the largest of the five complexes of the electron transport chain, mitochondrial dysfunction resulting from variants of MT-ND2 have been linked to body mass index (BMI) in adults and implicated in metabolic disorders including obesity, diabetes and hypertension.

Mitochondrial-derived peptides (MDPs). These peptides are key factors in retrograde mitochondrial signaling as well as mitochondrial gene expression. Compared to the human nuclear genome, mitochondria have a modest sized circular genome of ~16,570 bp, which ostensibly includes only 13 protein coding genes, which are all structural components of the electron transport chain system.

Mitochondrial DNA (mtDNA) replication and transcription starts are regulated by nuclear-encoded proteins and is thought to be transcribed as a single polycistronic precursor that is processed into individual genes by excising the strategically positioned 22 tRNAs (tRNA punctuation model), giving rise to two rRNAs and 13 mRNA.

The human mitochondrion has two promoters in the heavy strand (major and minor) in close proximity, and one in the light strand, thereby giving rise to three different single polycistronic transcripts. The heavy major promoter is responsible for 80% of all Mitochondrial RNA (mtRNA) transcripts. Although the entire gene is thought to be transcribed as a single transcript, the abundance of individual rRNA, tRNA, and mRNA transcripts varies greatly, and the rRNAs are the most abundant. This processing structure indicates an unexplored class of posttranscriptional processing in the mitochondria.

Importantly, many of the mRNA species identified from the mitochondria are discrete smaller length ones that do not map to the traditional mitochondrial protein encoding genes. For example, multiple such mRNAs are observed from the 16S rRNA. Parallel analysis of RNA ends (PARE) reveals a plethora of expected and unexpected cleavage sites have been discovered for the mitochondria. The majority of tRNAs and mRNA have distinct dominant cleavage sites at the 5' termini, but intragenic cleavage sites are especially abundant in rRNAs. Notably, there is compelling evidence from the emerging field of small peptides showing biologically active peptides of 11-32 amino acids in length which are encoded by small open reading frames (sORFs) from a polycistronic mRNA.

Mitochondria are thought to have transferred their genome to the host nucleus leaving chromosomal "doppelgangers", through the process of Nuclear Mitochondrial DNA-Transfer or nuclear insertions of mitochondrial origin (NUMTs). NUMTS come in various sizes from all parts of the mtDNA with various degrees of homology with the original sequences. Entire mtDNA can be found in the nuclear genome, although in most cases with substantial sequence degeneration. Most NUMTs are small insertions of <500 bp and only 12.85% are >1500 bp. The percentage identity is inversely correlated with size and the mean percentage between NUMTs and mtDNA is 79.2% with a range of 63.5% to 100% identity.

Diabetes mellitus. Diabetes is associated with continuous and pathologically elevated blood glucose concentration. Diabetes is divided into two major sub-classes: Type 1 (also known as Type I, juvenile diabetes, or Insulin-Dependent Diabetes Mellitus (IDDM)) and Type 2 (also known as Type II, adult onset diabetes, or Non-Insulin-Dependent Diabetes Mellitus (NIDDM)).

In normal, healthy subjects, glucose concentration in the human bloodstream is controlled within a relatively tight range (60-120 milligrams per deciliter of blood). Excessive blood glucose, or hyperglycemia, can eventually cause tissue damage due to the presence of excess glucose and buildup attachment to proteins in cells, tissues, and organs. This damage is thought to cause the diabetic complications of blindness, kidney failure, impotence, atherosclerosis, and increased vulnerability to infection.

Diabetes is usually diagnosed following the onset of excessive urination or excessive thirst, often accompanied by weight loss. Generally, a pre-diabetic individual refers to an adult with a fasting blood glucose level greater than 110 mg/dl but less than 126 mg/dl or a 2 hour PG reading of greater than 140 mg/dl but less than 200 mg/dl. A diabetic individual will possess a fasting blood glucose level greater than 126 mg/dl or a 2-hour PG reading of greater than 200 mg/dl. Impaired glucose tolerance is diagnosed in individuals that have fasting blood glucose levels less than those required for a diagnosis of diabetes, but have a plasma glucose response during the oral glucose tolerance test (OGTT) between normal and diabetics. Impaired glucose tolerance is considered a prediabetic condition, and impaired glucose tolerance is a strong predictor for the development of Type II diabetes mellitus Early intervention in individuals at risk of developing diabetes focuses on reducing the pathological hyperglycemia or impaired glucose tolerance to prevent or delay the progression towards diabetes and associated complications. Insulin, sulfonylureas, glucagon-like peptide-1 (GLP-1) receptor agonists are major classes of diabetes medicines prescribed today in the United States. Insulin is prescribed for both Type 1 and Type 2 diabetes, while sulfonylureas and GLP-1 agonists are usually prescribed for Type 2 diabetics. While sulfonylureas and GLP-1 agonists can stimulate natural insulin secretion and reduce insulin resistance, these compounds do not replace the function of insulin in metabolism. Eventually, a significant number of patients who receive sulfonylurea become resistant to it. Some Type II diabetics do not respond to sulfonylurea therapy. Of patients who do respond to initial treatment with sulfonylureas, 5-10% are likely to experience a loss of sulfonylurea effectiveness after about ten years.

In addition, many anti-diabetic agents, for example, sulfonylureas and Thiazolidinediones, have an undesired side effect of increasing body weight. Increased body weight in patients with prediabetic conditions or with diagnosed Type II diabetes mellitus can cause deleterious effects due to accentuation of the metabolic and endocrine dysregulation. Obesity per se is a significant risk factor for the development and progressive worsening of Type II diabetes mellitus. There is also some concern over the safety profile of GLP-1 agonists due to proliferative effects in the pancreas. Thus it is desirable to have an anti-diabetic agent which maintains or lowers body weight, maintains efficacy, and with minimal side effects on normal homeostatic processes.

As described herein, the Inventors have discovered a novel, mitochondrial encoded open reading frame that leads to the production of a new polypeptide that is called MENTSH (Mitochondrial-derived peptide Encoded in the ND-Two Subunit of Humans)

Using a mitochondrial genome-wide association study, the Inventors have correlated a specific small nucleotide polymorphism that disrupts the MENTSH gene with an increase in obesity and diabetes. Interestingly, this polymorphism is highly prevalent in Mexican-Americans and could explain that population's increased chance of diabetes in the presence of obesity. Interestingly, a "C/G" mutation is synonymous (silent) with respect to the ND2 gene, but disrupts the start codon of the MENTSH peptide, as a consequence of the polycistronic nature of mitochondrial transcript processing. In the mitochondria, the nucleotides ATT can initiate a start codon. This SNP changes the ATT to ACT, which no longer acts as a start codon causing the protein to not be generated. The "C/G" mutation in human subjects therefore has the effect of a MENTSH knockout, accounting at least in part for the observed association.

Additionally, the Inventors discovered that in vitro administration of MENTSH increases insulin secretion, decreases fat accumulation and improves glucose uptake in muscle cell. These effects may be mediated by AKT activation in specific cell types. Unique metabolomics signature in MENTSH-treated mice can serve as a pharmacodynamics marker for MENTSH therapy. Antibodies were generated against MENTSH and the Inventors created an ELISA assay for MENTSH that can be used to assess MENTSH deficiency and monitor MENTSH therapy.

In vivo studies further revealed that administration of MENTSH improves glucose tolerance of mice fed a high-fat/"western" diet, thus serving as a novel diabetes therapy and decreases bodyweight in mice fed a high-fat diet, thus serving as a novel obesity therapy.

By generating analogs of MENTSH, the Inventors were able to further enhance or abrogate activity relative to the natural peptide.

Described herein is a mitochondrial peptide. In one embodiment, the mitochondrial peptide includes a peptide with the amino acid sequence MKPNPATQNLSMLLNYPH (SEQ ID NO:97), analog or derivative thereof.

In one embodiment, the mitochondrial peptide is 14, 15, 16, 17, 18, 19, 20, 21, 22, 23, or 24 amino acids in length. In a particular embodiment, the mitochondrial peptide is 18 amino acids in length. In one embodiment, the mitochondrial peptide includes a synthetic amino acid. In one embodiment, the mitochondrial peptide possesses less than about 25%, 30%, 35%, 40%, 45%, 50%, 55%, 60%, 65%, 70%, 75%, 80%, 85% or more percentage identity to MKPNPATQNLSMLLNYPH (SEQ ID NO:97). One of ordinary skill in the art can establish percentage identity according to methods known in the art, including establishing a comparison window between a reference amino acid sequence and a second amino sequence, to establish the degree of percentage identity. Examples are shown in Table 1.

In other embodiments, the mitochondrial peptide possesses a post-translational modification or other type of modification such as an artificial modification. In various embodiments, this includes for example, pegylation, fatty-acid conjugation lipdation, repeat polypeptide extension, IgG-Fc, CPT, HSA, ELP, transferrin, or albumin modification, among others. For example, modifications could include formylation at methionine position 1, phosphorylation at threonine position 7, phosphorylation at serine position 11, phosphorylation of tyrosine at position 16, or acetylation of lysine at position 2 of SEQ ID NO: 97, or corresponding positions in analogs or derivatives thereof exemplified by sequences SEQ ID NO: 1 to SEQ ID NO: 96 as shown in Table 1.

In one embodiment, the mitochondrial peptide increases insulin secretion. In one embodiment, the mitochondrial peptide decreases glucagon levels. In one embodiment, the mitochondrial peptide improves glucose response. In one embodiment, the mitochondrial peptide decreases fat accumulation. In one embodiment, the mitochondrial peptide improves glucose uptake in cells, including for example, muscle cells. In one embodiment, the mitochondrial peptide improves glucose tolerance.

Described herein is a peptide. In various embodiments, the peptide is 14, 15, 16, 17, 18, 19, 20, 21, 22, 23, or 24 amino acids in length. In various embodiments, the peptide at position 1 (i.e., first N-terminal amino acid) is X1, position 2 is (X2) and so on (X3, X4, 5, X6, etc.), wherein X1, X2, X3, X4, X5, X6, etc. is selected from a group consisting of a natural or synthetic amino acid. In various embodiments, the peptide is one of SEQ ID NO: 1 to SEQ ID NO: 35. In various embodiments, the peptide is one of SEQ ID NO: 36 to SEQ ID NO: 42. In various embodiments, the peptide is one of SEQ ID NO: 43 to SEQ ID NO: 96. In other embodiments, the mitochondrial peptide possesses a post-translational modification or other type of modification such as an artificial modification. In various embodiments, this includes for example, pegylation, fatty-acid conjugation lipdation, repeat polypeptide extension, IgG-Fc, CPT, HSA, ELP, transferrin, or albumin modification, among others. For example, modifications could include formylation at methionine X1, phosphorylation at threonine X7, phosphorylation at serine X11, phosphorylation of tyrosine at X16, or acetylation of lysine at X2 of SEQ ID NO: 97, or corresponding X1,X2, X3, X4, X5, X6, etc. positions in analogs or derivatives thereof exemplified by sequences SEQ ID NO: 1 to SEQ ID NO: 96 as shown in Table 1. In various embodiments, the peptide possesses less than about 25%, 30%, 35%, 40%, 45%, 50%, 55%, 60%, 65%, 70%, 75%, 80%, 85% or more percentage identity to MKPNPATQNLSMLLNYPH (SEQ ID NO:97).

Described herein is a method of treating a disease and/or condition using a mitochondrial peptide including the steps of selecting a subject in need of treatment, and administering a quantity of the mitochondrial peptide to a subject in need of treatment. In one embodiment, the mitochondrial peptide is a MKPNPATQNLSMLLNYPH (SEQ ID NO:97), analog or derivative thereof. 14, 15, 16, 17, 18, 19, 20, 21, 22, 23, or 24 amino acids in length. In one embodiment, the mitochondrial peptide is 18 amino acids in length.

In one embodiment, the quantity of the mitochondrial peptide administered is a therapeutically effective amount of the mitochondrial peptide. In one embodiment, the subject is a mammal. In one embodiment, the subject is a human.

TABLE 1

Examples of MENTSH analogs

| | Sequence |
|---|---|
| Original | MKPNPATQNLSMLLNYPH (SEQ ID NO: 97) |
| 1 | AKPNPATQNLSMLLNYPH (SEQ ID NO: 1) |
| 2 | MAPNPATQNLSMLLNYPH (SEQ ID NO: 2) |
| 3 | MKANPATQNLSMLLNYPH (SEQ ID NO: 3) |
| 4 | MKPAPATQNLSMLLNYPH (SEQ ID NO: 4) |
| 5 | MKPNAATQNLSMLLNYPH (SEQ ID NO: 5) |
| 6 | MKPNPATQNLSMLLNYPH (SEQ ID NO: 6) |
| 7 | MKPNPAAQNLSMLLNYPH (SEQ ID NO: 7) |
| 8 | MKPNPATANLSMLLNYPH (SEQ ID NO: 8) |
| 9 | MKPNPATQALSMLLNYPH (SEQ ID NO: 9) |
| 10 | MKPNPATQNASMLLNYPH (SEQ ID NO: 10) |
| 11 | MKPNPATQNLAMLLNYPH (SEQ ID NO: 11) |
| 12 | MKPNPATQNLSALLNYPH (SEQ ID NO: 12) |
| 13 | MKPNPATQNLSMALNYPH (SEQ ID NO: 13) |
| 14 | MKPNPATQNLSMLANYPH (SEQ ID NO: 14) |
| 15 | MKPNPATQNLSMLLAYPH (SEQ ID NO: 15) |
| 16 | MKPNPATQNLSMLLNAPH (SEQ ID NO: 16) |
| 17 | MKPNPATQNLSMLLNYAH (SEQ ID NO: 17) |
| 18 | MKPNPATQNLSMLLNYPA (SEQ ID NO: 18) |
| 19 | KPNPATQNLSMLLNYPH (SEQ ID NO: 19) |
| 20 | {Nle}KPNPATQNLS{Nle}LLNYPH (SEQ ID NO: 20) |
| 21 | MKPNPATQN (SEQ ID NO: 21) |
| 22 | PATQNLSML (SEQ ID NO: 22) |
| 23 | NLSMLLNYP (SEQ ID NO: 23) |

TABLE 1-continued

Examples of MENTSH analogs

| | Sequence |
|---|---|
| 24 | LLNYPH (SEQ ID NO: 24) |
| 25 | MKANAATQNLSMLLNYAH (SEQ ID NO: 25) |
| 26 | MKGNGATQNLSMLLNYGH (SEQ ID NO: 26) |
| 27 | MKANAATQNLSMLLNYPH (SEQ ID NO: 27) |
| 28 | MKPNAATQNLSMLLNYAH (SEQ ID NO: 28) |
| 29 | MKANPATQNLSMLLNYAH (SEQ ID NO: 29) |
| 30 | MKPNPADQNLDMLLNDPH (SEQ ID NO: 30) |
| 31 | MKPNPADQNLDMLLNYPH (SEQ ID NO: 31) |
| 32 | MKPNPATQNLDMLLNDPH (SEQ ID NO: 32) |
| 33 | MKPNPADQNLSMLLNDPH (SEQ ID NO: 33) |
| 34 | MKPNPADQNLSMLLNYPH (SEQ ID NO: 34) |
| 35 | MKPNPATQNLDMLLNYPH (SEQ ID NO: 35) |
| 36 | MKPNPATQNLSMLLNDPH (SEQ ID NO: 36) |
| 37 | MKPNPAGQNLGMLLNGPH (SEQ ID NO: 37) |
| 38 | MKPNPAGQNLGMLLNYPH (SEQ ID NO: 38) |
| 39 | MKPNPATQNLGMLLNGPH (SEQ ID NO: 39) |
| 40 | MKPNPAGQNLSMLLNGPH (SEQ ID NO: 40) |
| 41 | MKPNPAGQNLSMLLNYPH (SEQ ID NO: 41) |
| 42 | MKPNPATQNLGMLLNYPH (SEQ ID NO: 42) |
| 43 | MKPNPATQNLSMLLNGPH (SEQ ID NO: 43) |
| 44 | MKPNPSTQNTSMTTNQPH (SEQ ID NO: 44) |
| 45 | MKPNPSTQNTSMTTNYPH (SEQ ID NO: 45) |
| 46 | MKPNPSTQNTSMILNQPH (SEQ ID NO: 46) |
| 47 | MKPNPSTQNTSMLINQPH (SEQ ID NO: 47) |
| 48 | MKPNPATQNTSMTNQPH (SEQ ID NO: 48) |
| 49 | MKPNPSTQNTSMILNYPH (SEQ ID NO: 49) |
| 50 | MKPNPATQNTSMTTNYPH (SEQ ID NO: 50) |
| 51 | MKPNPATQNLSMTTNQPH (SEQ ID NO: 51) |
| 52 | MKPNPSTQNLSMLINQPH (SEQ ID NO: 52) |
| 53 | MKPNPSTQNTSMLSNQPH (SEQ ID NO: 53) |
| 54 | MKPNPATQNTSMLINQPH (SEQ ID NO: 54) |
| 55 | MKPNPSTQNLSMLNQPH (SEQ ID NO: 55) |
| 56 | MKPNPSTQNLSMTTNYPH (SEQ ID NO: 56) |
| 57 | MKPNPATQNTSMILNQPH (SEQ ID NO: 57) |
| 58 | MKPNPSTQNTSMLINYPH (SEQ ID NO: 58) |
| 59 | MKPNPSTQNTSMLLNYPH (SEQ ID NO: 59) |
| 60 | MKPNPSTQNLSMILNYPH (SEQ ID NO: 60) |
| 61 | MKPNPSTQNLSMLINYPH (SEQ ID NO: 61) |
| 62 | MKPNPSTQNLSMLLNQPH (SEQ ID NO: 62) |
| 63 | MKPNPLTQNTSMILNYPH (SEQ ID NO: 63) |
| 64 | MKPNPLTQNZSMLINYPH (SEQ ID NO: 64) |
| 65 | MKPNPATQNTSMLLNQPH (SEQ ID NO: 65) |
| 66 | MKPNPLTQNLSMTTNYPH (SEQ ID NO: 66) |
| 67 | MKPNPLTQNLSMILNQPH (SEQ ID NO: 67) |
| 68 | MKPNPATQNLSMLINQPH (SEQ ID NO: 68) |
| 69 | MKPNPSTQNLSMLLNYPH (SEQ ID NO: 69) |
| 70 | MKPNPATQNTSMLLNYPH (SEQ ID NO: 70) |
| 71 | MKPNPATQNLSMILNYPH (SEQ ID NO: 71) |
| 72 | MKPNPATQNLSMLINYPH (SEQ ID NO: 72) |
| 73 | MKPNPATQNLSMLLNQPH (SEQ ID NO: 73) |
| 74 | AKPNPATANLSMLLNYPA (SEQ ID NO: 74) |
| 75 | MAPNPATQNASMLLNYAH (SEQ ID NO: 75) |
| 76 | MKPAPATANLSMLLNYAH (SEQ ID NO: 76) |
| 77 | MKPAPATQALSMLLAYPH (SEQ ID NO: 77) |
| 78 | MKPNAATQALSMLANYPH (SEQ ID NO: 78) |
| 79 | MAPNPAAQNLSALLNYPH (SEQ ID NO: 79) |
| 80 | MKPNPATQNLSMALAYAH (SEQ ID NO: 80) |
| 81 | AKPAPAAQNLSMLLNYPH (SEQ ID NO: 81) |
| 82 | MKPNPATQNLSMALAYPA (SEQ ID NO: 82) |
| 83 | MKPNAATANLAMLLNYPH (SEQ ID NO: 83) |
| 84 | MKPNPATQALSMALNAPH (SEQ ID NO: 84) |
| 85 | MAPNAATQNASMLLNYPH (SEQ ID NO: 85) |
| 86 | AKANPATQNLSMLLNYPH (SEQ ID NO: 86) |
| 87 | MAPAPATQNLSMLLNYPH (SEQ ID NO: 87) |
| 88 | MKPAPAAQNLSMLLNYPH (SEQ ID NO: 88) |
| 89 | MKPNAAAQNLSMLLNYPH (SEQ ID NO: 89) |
| 90 | MKPNPATANASMLLNYPH (SEQ ID NO: 90) |
| 91 | MKPNPATQALAMLLNYPH (SEQ ID NO: 91) |
| 92 | MKPNPATQNASALLNYPH (SEQ ID NO: 92) |
| 93 | MKPNPATQNLAMALNYPH (SEQ ID NO: 93) |
| 94 | MKPNPATQNLSALANYPH (SEQ ID NO: 94) |
| 95 | MKPNPATQNLSMALAYPH (SEQ ID NO: 95) |
| 96 | MKPNPATQNLSMLANAPH (SEQ ID NO: 96) |

In various embodiments, disease and/or condition suitable for treatment with the mitochondrial peptide or analogue composition described include those disorders characterized by reduced blood insulin levels, or reduced number or function of pancreatic beta islet cells. In various embodiments, the disease and/or condition includes type 1 and type 2 diabetes, gestational diabetes, pre-diabetes, insulin resistance, metabolic syndrome, and impaired glucose tolerance. The compositions of the invention can be used prophylactically, e.g., for individuals with a genetic predisposition for diabetes. In various embodiments, disease and/or condition suitable for treatment with the mitochondrial peptide or analogue composition described includes obesity. In other embodiments, the disease and/or condition includes diabetic complications such as retinopathy, neuropathy, renal diseases. In other embodiments, the disease and/or condition includes dyslipidemia.

In various embodiments, the subject is prediabetic. In various embodiments, the subject is diabetic. In various embodiments, the subject is obese or overweight. In various embodiments, the subject is Hispanic, including individuals self-identifying as Hispanic. In various embodiments, the subject is Native American, including individuals self-identifying as Native American. In various embodiments, the subject is South American including individuals self-identifying as South American. In various embodiments, the subject is Central American, including individuals self-identifying as Central American. In various embodiments, the subject is a carrier of the SNP Rs28357981. This includes, for example, a "G" or "C" allelic mutation abrogating expression of the open reading frame encoding MKPNPATQNLSMLLNYPH (SEQ ID NO:97). In various embodiments, the subject does not express the peptide MKPNPATQNLSMLLNYPH (SEQ ID NO:97). In various embodiments, the subject expresses low amounts of MKPNPATQNLSMLLNYPH (SEQ ID NO:97) relative to a healthy normal subject without diabetes and/or obesity. In other embodiments, the subject possesses a metabolic signature of low MENTSH activity. In other embodiments, the subject possesses a metabolic signature of high MENTSH activity. In various embodiments, the subject is administered a dominant negative analog and/or derivative of MENTSH, including for example, one of SEQ ID NO: 36 to SEQ ID NO: 42 listed in Table 1. In other embodiments, the disease and/or condition is cancer, Alzheimer's, and/or atherosclerosis.

Described herein is a method of diagnosing an individual for a disease and/or condition. In various embodiments, the method includes selecting a subject, detecting the presence, absence, or expression level of one or more biomarkers, and diagnosing the subject for a disease and/or condition, based on the presence, absence, or expression level of the one or more biomarkers. In various embodiments, the biomarker includes a mitochondrial peptide. In various embodiments, the biomarker includes MKPNPATQNLSMLLNYPH (SEQ ID NO:97). For example, the subject may be diagnosed with prediabetes, diabetes, and/or obesity if expressing a low amount of MKPNPATQNLSMLLNYPH (SEQ ID NO:97) relative to a healthy normal subject without diabetes and/or obesity. In various embodiments, detection of the presence, absence, or expression level of the biomarker includes antibody detection of the one of or more biomarkers, including the use of, for example, a monoclonal antibody, polyclonal antibody, antisera, other immunogenic detection, and mass spectrometry detection methods.

In another embodiment, the biomarker includes a single nucleotide polymorphism (SNP). In various embodiments, the SNP is Rs28357981. This includes, for example, a "G/C" allelic mutation abrogating expression of the open reading frame encoding MKPNPATQNLSMLLNYPH (SEQ ID NO:97), wherein the absence of MKPNPATQNLSMLLNYPH (SEQ ID NO:97) diagnoses the subject for a subtype of prediabetes, diabetes, and/or obesity. One of ordinary skill in the art is apprised of the methods capable of SNP detection.

In various embodiments, the disease and/or condition include those characterized by reduced or increased blood insulin levels, or reduced number or function of pancreatic beta islet cells. In various embodiments, the disease and/or condition includes type 1 and type 2 diabetes, gestational diabetes, pre-diabetes, insulin resistance, metabolic syndrome, and impaired glucose tolerance. In various embodiments, disease and/or condition includes obesity. In other embodiments, the disease and/or condition includes diabetic complications such as retinopathy, neuropathy, renal diseases. In other embodiments, the disease and/or condition includes dyslipidemia.

In various embodiments, the subject is prediabetic. In various embodiments, the subject is diabetic. In various embodiments, the subject is obese or overweight. In various embodiments, the subject is Hispanic, including individuals self-identifying as Hispanic. In various embodiments, the subject is Native American, including individuals self-identifying as Native American. In various embodiments, the subject is South American including individuals self-identifying as South American. In various embodiments, the subject is Central American, including individuals self-identifying as Central American.

The present invention further provides a method of enhancing efficacy of a treatment disease and/or condition using a mitochondrial peptide, including the steps of selecting a subject in need of treatment, and administering a quantity of the mitochondrial peptide to a subject receiving treatment a disease and/or condition, wherein the mitochondrial peptide enhancing the efficacy of the disease and/or condition, thereby enhancing efficacy of the treatment. In one embodiment, the mitochondrial peptide is administered simultaneously with a composition capable of treating an inflammatory disease and/or condition. In one embodiment, the mitochondrial peptide is administered sequentially, before or after administration, of a composition capable of treating a disease and/or condition. In one embodiment, the subject is a human. For example, the mitochondrial peptides and analog compositions of the invention can be co-administered with other therapeutic agents for the treatment of diabetes. Co-administration can be simultaneous, e.g., in a single pharmaceutical composition or separate compositions. The compositions of the invention can also be administered separately from the other therapeutic agent(s), e.g., on an independent dosing schedule.

In various embodiments, the present invention further provides a pharmaceutical composition. In one embodiment, the pharmaceutical composition includes a mitochondrial peptide and a pharmaceutically acceptable carrier. In one embodiment, the mitochondrial peptide is MKPNPATQNLSMLLNYPH (SEQ ID NO:97). In some embodiments, the bioactive mitochondrial peptide is as small as 6-9 amino-acids, as well as some that are 14, 15, 16, 17, 18, 19, 20, 21, 22, 23, or 24 amino acids in length. In one embodiment, the mitochondrial peptide is 18 amino acids in length. In one embodiment, the mitochondrial peptide in the pharmaceutical composition includes a therapeutically effective amount of the mitochondrial peptide. In one embodiment, pharmaceutical composition includes one or more mitochondrial peptides and a pharmaceutically acceptable carrier.

In various embodiments, the present invention further provides a method of manufacturing a mitochondrial peptide. In one embodiment, the method of manufacturing includes the steps of providing one or more polynucleotides encoding a mitochondrial peptide, expressing the one or more polynucleotides in a host cell, and extracting the mitochondrial peptide from the host cell. In one embodiment, the method of manufacturing includes the steps of expressing the one or more polynucleotides in a host cell, and extracting the mitochondrial peptide from the host cell. In one embodiment, the one or more polynucleotides are a sequence encoding MKPNPATQNLSMLLNYPH (SEQ ID NO:97), or a mitochondrial peptide possessing less than about 25%, 30%, 35%, 40%, 45%, 50%, 55%, 60%, 65%, 70%, 75%, 80%, 85% or more percentage identity to MKPNPATQNLSMLLNYPH (SEQ ID NO:97). In various embodiments, the polynucleotides possess less than about 25%, 30%, 35%, 40%, 45%, 50%, 55%, 60%, 65%, 70%, 75%, 80%, 85% or more percentage identity to attaaaccaaacccagctacgcaaaatcttagcatactcctcaattacccacatagg (SEQ ID NO:98).

In another embodiment, the method of manufacturing includes the steps of peptide synthesis using liquid-phase synthesis or solid-phase synthesis. In one embodiment, the solid-phase synthesis is Fmoc or BOC synthesis.

Example 1

Discovery

The Inventors performed a genome wide association study (GWAS) for 9,825 Health and Retirement Study (HRS) participants to examine the association between mitochondrial variants and glycosylated hemoglobin HbA1ac. The GWAS was run for 68 mitochondrial SNPs with minor allele frequencies>0.01. Models were adjusted for age and population stratification (the first 4 Eigenvalues). One SNP (MitoT4978C, also known as Rs28357981) was found to be significantly associated with HbA1ac after adjusting for multiple-testing (P=4.9E-04, Bonferroni P=0.03) (FIG. 1).

Next, examining the association between this SNP and diabetes diagnosis revealed that the SNP is associated with a 38% increase in the risk of diabetes, but not associated with heart disease or hypertension Example 2

Ethnicity Effects

Interestingly, the SNP is far more common in participants who self-identify as Hispanic (MAFHispanic=18.65 vs. MAFNon-Hispanic=0.27). When the association between MitoT4978C and HbA1ac was examined by Hispanicity, results remained significant.

Example 3

Obesity

Figure 2:
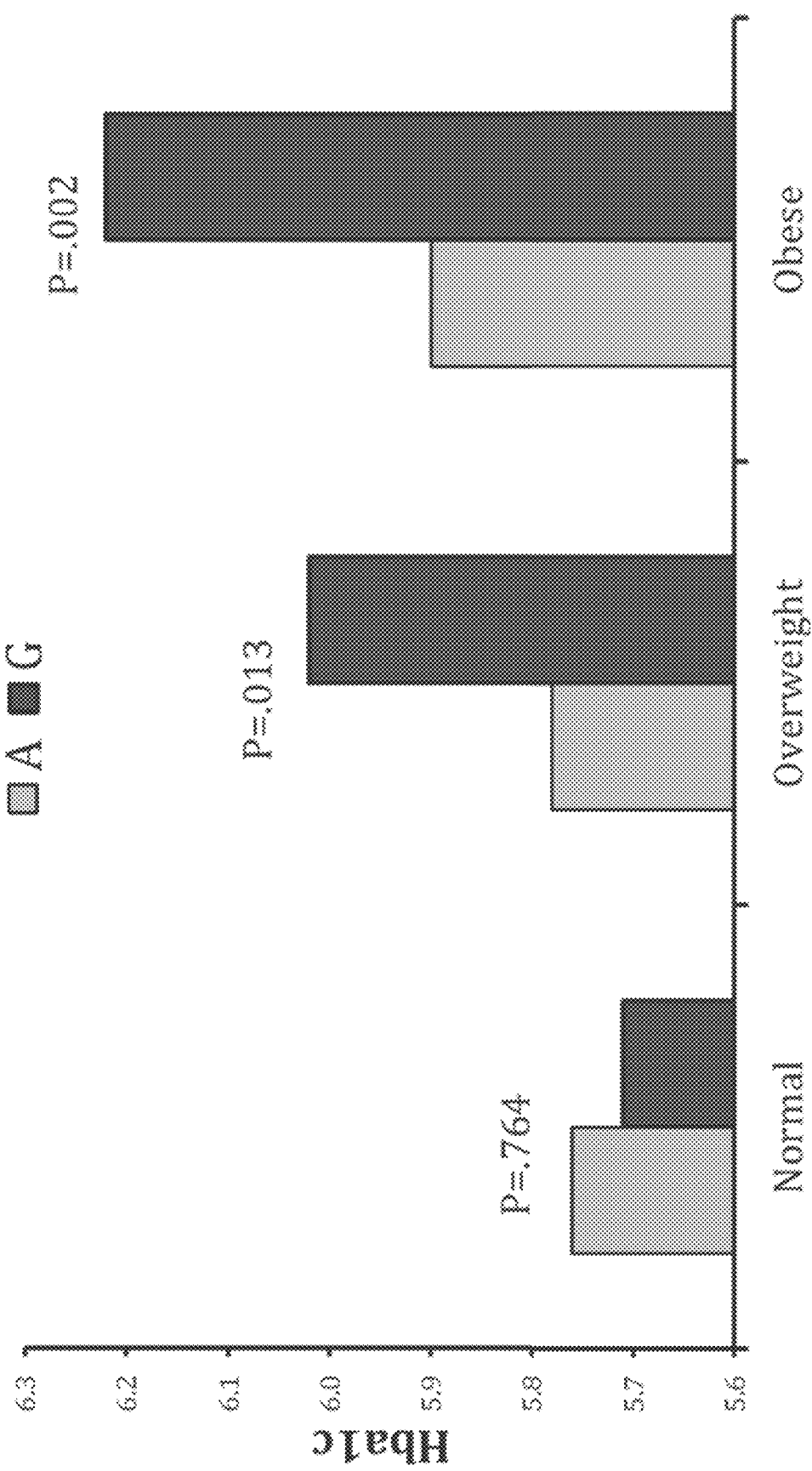
FIG. 2. Interaction between MitoT4978C and BMI Categories. The association between MitoT4978C and Hb1ac by BMI found a significant SNP X BMI interaction. Results showed that as BMI increases the effect of the SNP on Hba1c increases.
Figure 3:
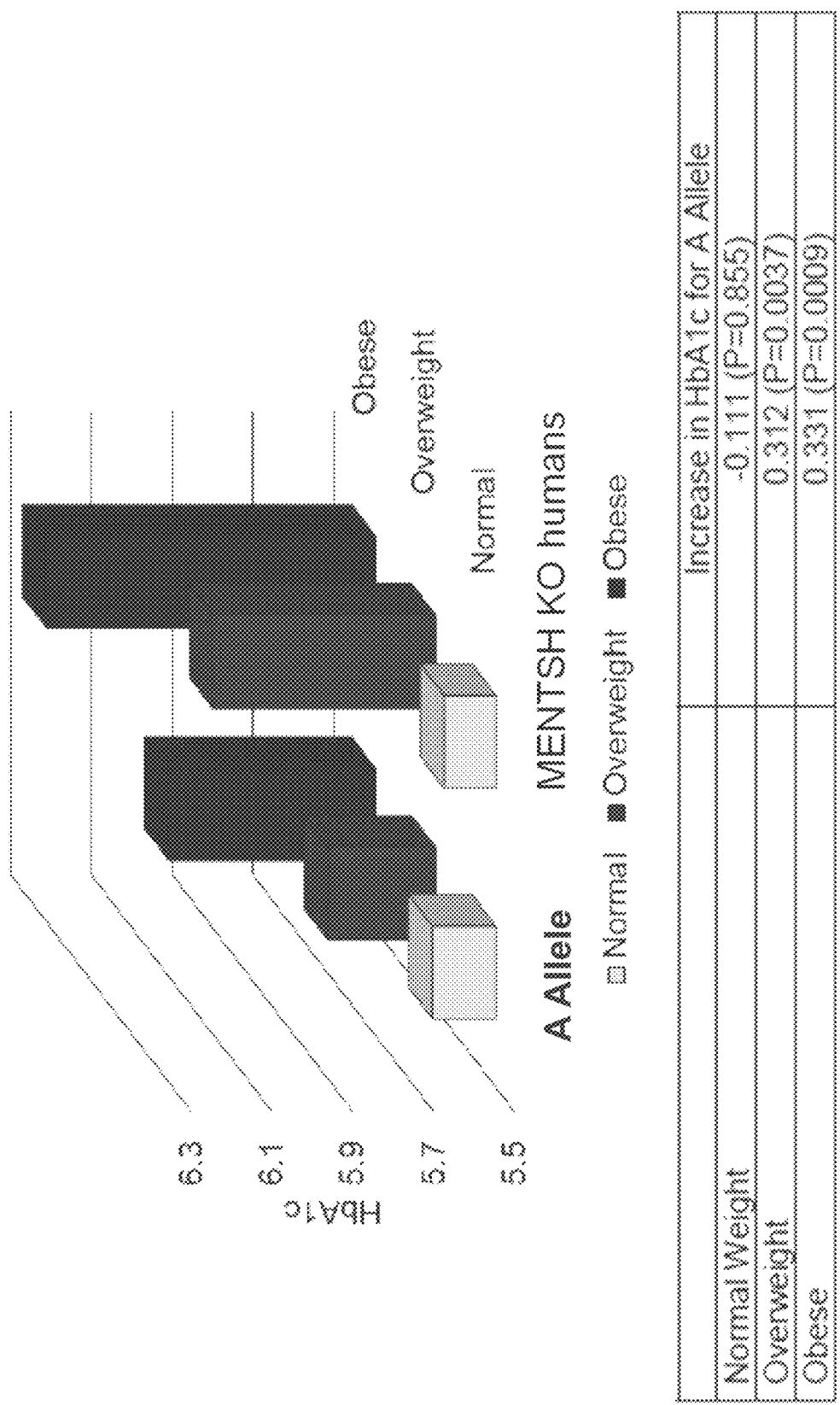
FIG. 3. MENTSH deficiency synergizes with obesity to cause diabetes.

When examining the association between MitoT4978C and Hb1ac by body mass index (BMI), the Inventors found a significant SNP X BMI Interaction (FIG. 2). Specifically, results showed that as BMI increases the effect of the SNP on Hba1c increases. Even after adjusting for age, sex, race, and BMI the risk of having diabetes is almost 2-fold higher in the G/C allele group (OR: 1.90, p<0.0001) (FIG. 3).

TABLE 2

Allelic distribution in normal weight, overweight and obese subjects

|  | Increase in HbA1c for A Allele |
| --- | --- |
| Normal Weight | −0.111 (P = 0.855) |
| Overweight | 0.312 (P = 0.0037) |
| Obese | 0.331 (P = 0.0009) |

Example 4

HbA1c and Diabetes Results for MitoT4978C (Rs28357981)

All analyses were adjusted for age, sex, population stratification (PC14), education, BMI, and smoking. Results show that having the minor allele (A) is associated with 0.12 higher HbA1ac and a suggestive 15% increase in diabetes risk. When examining these relationships by race/ethnicity, no significant associations are found for non-Hispanic whites, however, the A allele is associated with 0.56 higher HbA1ac and 82% increase in diabetes among non-Hispanic blacks, and 0.12 higher HbA1ac and 18% increase in diabetes (suggestive) among Hispanics. Results also show that HbA1ac is higher among persons not diagnosed with diabetes and those diagnosed (suggestive significance). SNP Rs28357981 is located in the mitochondrial ND2gene.

TABLE 3

HbA1c and diabetes results for MitoT4978C (rs28357981)

| Effect of A allele | All Race/ Ethnic | Non-Hispanic White | Non-Hispanic Black | Hispanics |
| --- | --- | --- | --- | --- |
| HbA1c (Beta Coefficients) | 0.121 (P = 4.0E−4) | −0.039 (P = 0.699) | 0.590 (P = 0.001) | 0.123 (P = 0.025) |
| Diabetes (Odds Ratio) | 1.15 (P = 0.069) | 0.95 (0.903) | 1.82 (P = 0.037) | 1.18 (P = 0.053) |

TABLE 4

HbA1c Results for MitoT4978C (rs28357981) By Diabetes Status

| Effect of A allele | Never Diagnosed with Diabetes | Diagnosed with Diabetes |
| --- | --- | --- |
| HbA1C (Beta Coefficients) | 0.061 (P = 0.012) | 0.134 (P = 0.112) |

TABLE 5

Diabetes Results for MitoT4978C (rs28357981)

|  | Odds Ratio (P-Value) |
| --- | --- |
| No Diabetes (n = 7,453) | Reference category |
| Undiagnosed Diabetes (n = 248) | 0.369 (0.073) |
| Diagnosed Diabetes (n = 2,608) | 0.216 (0.018) |

Example 5

MENTSH—MDP Encoded in the ND-Two Subunit of Humans

Figure 4:
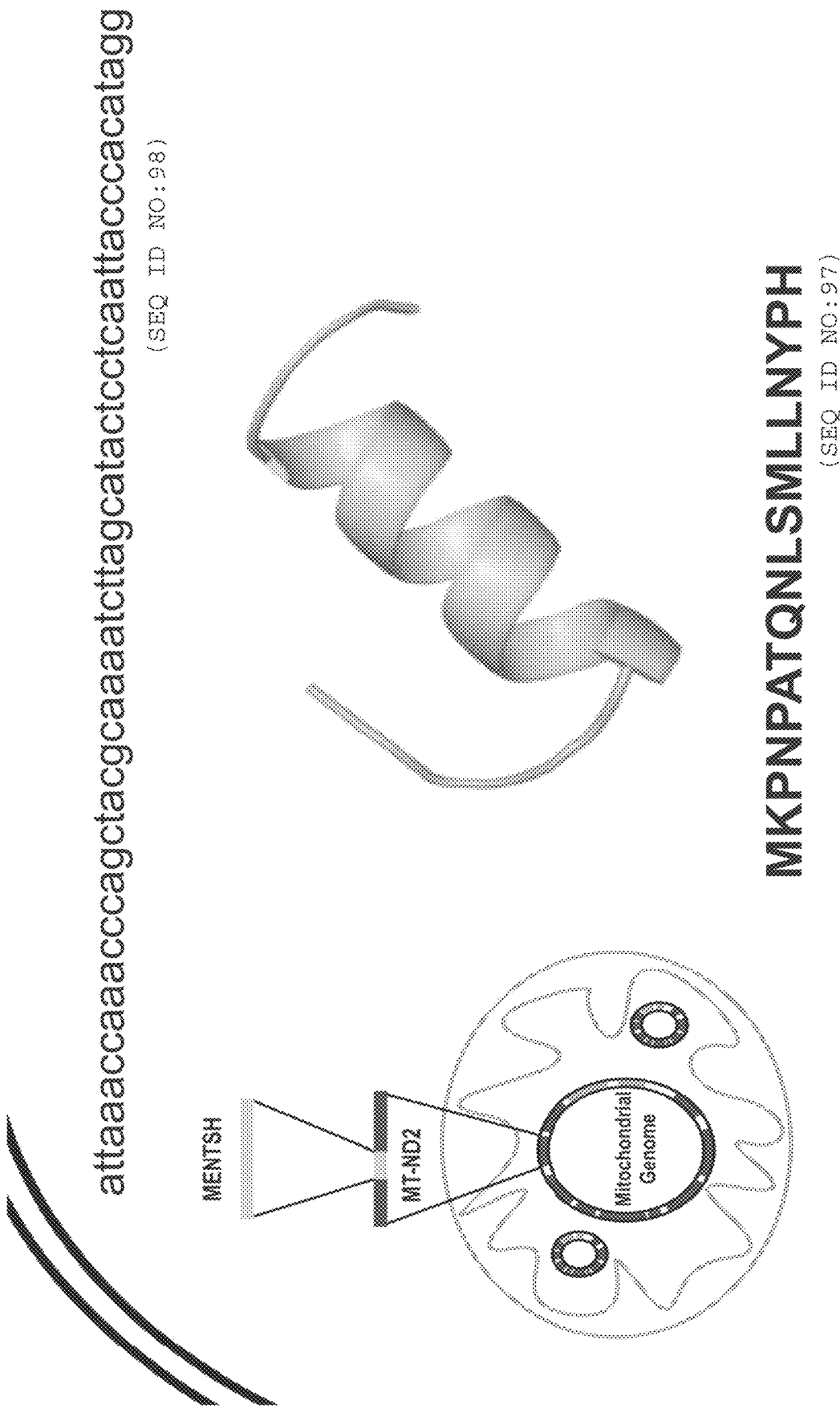
FIG. 4. MENTSH nucleic acid sequence (SEQ ID NO:98) and amino acid peptide sequence (SEQ ID NO:97). SNP Rs28357981 is within an open reading frame encoding a MDP—Mitochondrial Derived Peptide within the ND2 gene. While not affecting ND2 expression, presence of this SNP with a "C" mutation disrupts the start codon of MENTSH peptide based on the polycistronic structure of mitochondrial transcript processing. In the mitochondria, the nucleotides ATT can initiate a start codon. This SNP changes the ATT to ACT, which no longer acts as a start codon causing the protein to not be generated.

Focus on the SNP Rs28357981 revealed an open reading frame encoding a MDP-Mitochondrial Derived Peptide (and translated in the mitochondria) (FIG. 4). There is 2×expression increase of MENTSH mutation frequency in diabetics when controlling for age, sex, race, and BMI, which is prevalent in 18.5% of Hispanics and 0.3% in non-Hispanics. Interestingly, a "C" mutation is synonymous (silent) with respect to the ND2 gene, but disrupts the start codon of MENTSH peptide, as a consequence of the polycistronic nature of mitochondrial transcript processing. The "G" mutation in human subjects therefore has the effect of a MENTSH knockout, accounting at least in part for the observed association.

Further investigation revealed that the mRNA is distinct from, but partially homologous to, a portion of a theoretical gene named GREBP (115-aa)—that is encoded from a NUMT in chromosome-1. However, that gene does not encode the small MENTSH peptide that is 18 amino acids in length.

Example 6

MENTSH Increase Insulin Secretion in Ins-1 Cells

Figure 5:
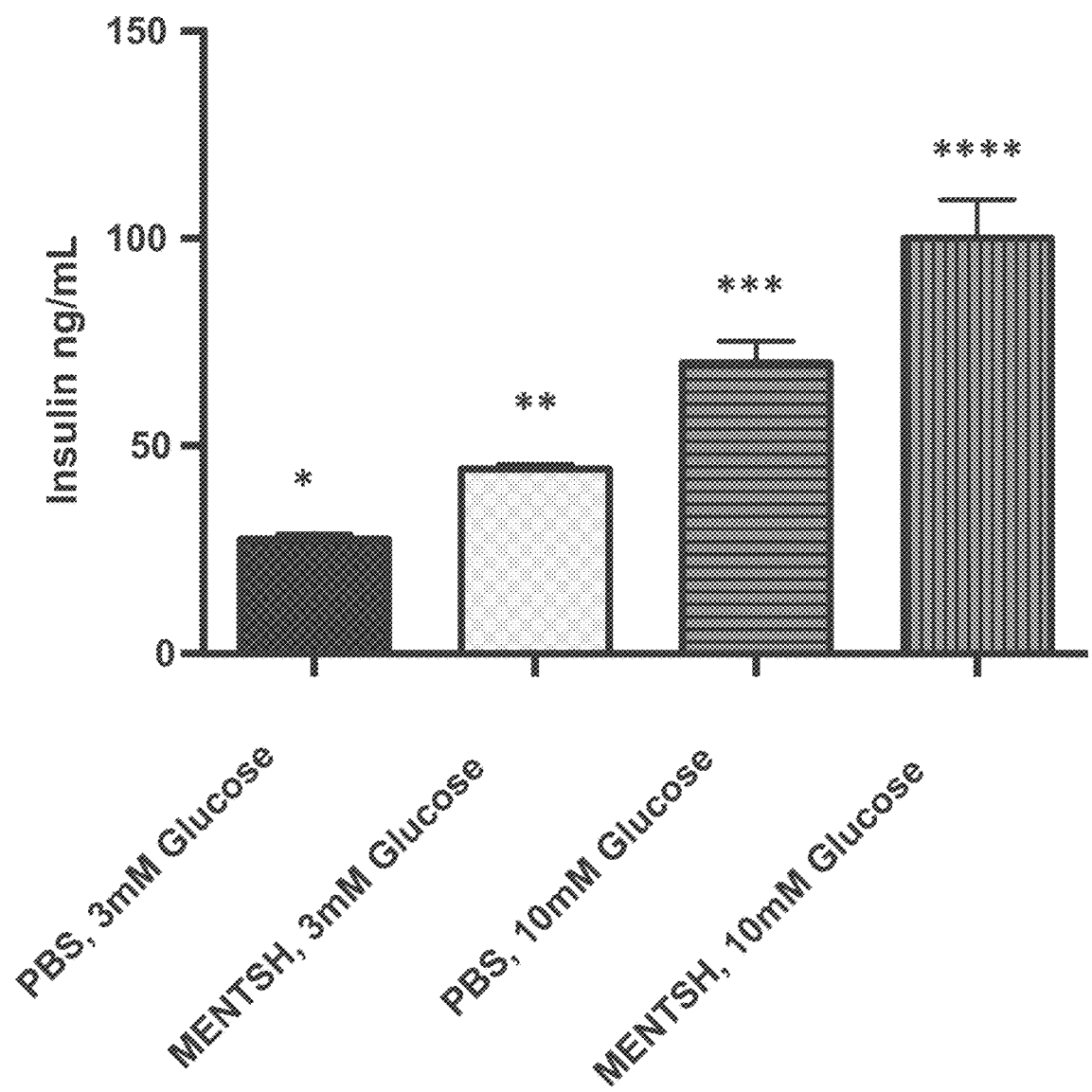
FIG. 5. MENTSH increase insulin secretion in ins-1 cells. Administration of MENTSH peptide to rat pancreatic ins-1 cells was capable of increasing insulin secretion in a statistically significant manner compared to untreated cells and was capable of further increasing insulin secretion in the presence of glucose addition FIG. 6. MENTSH decreases fat accumulation in vitro in 3T3 adipocytes.

In vitro, it was observed that addition of MENTSH peptide to rat pancreatic ins-1 cells was capable of increasing insulin secretion in a dose dependent manner and in a statistically significant manner when compared to glucose addition (FIG. 5).

Example 7

MENTSH Decreases Fat Accumulation In Vitro in 3T3 Adipocytes

Figure 6:
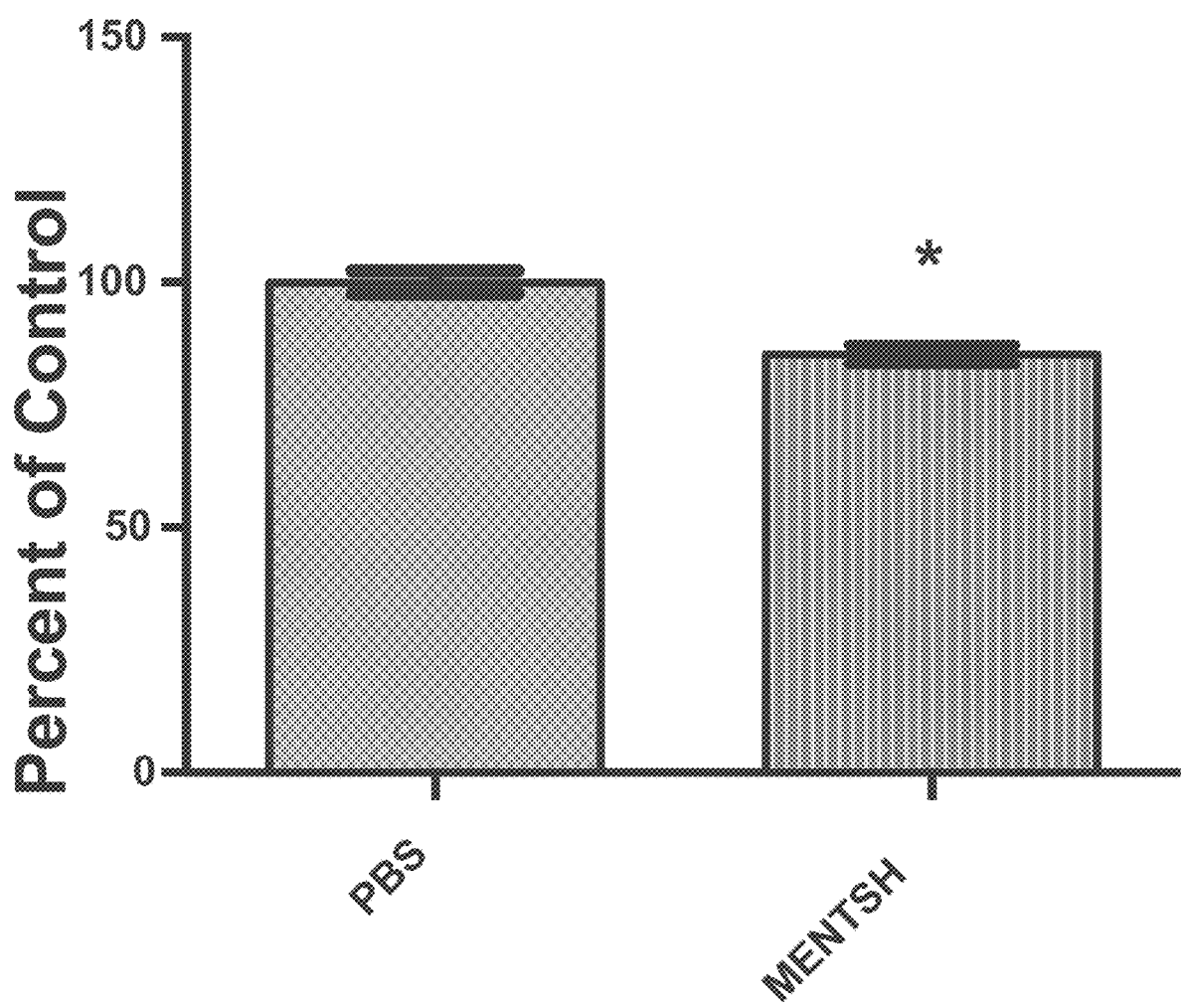

In vitro, addition of MENTSH peptide was capable of decreasing fat accumulation in 3T3 adipocytes (FIG. 6).

Example 8

MENTSH Rapidly Activates Signal Transduction in a Cell-Specific Manner

Figure 7:
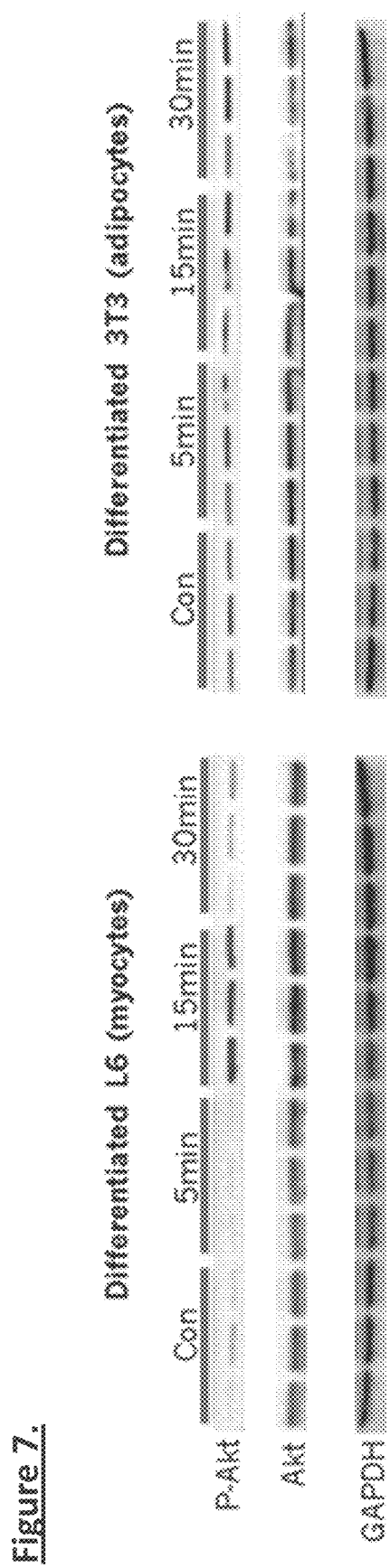
FIG. 7. MENTSH rapidly activates signal transduction in a cell-specific manner. These observed effects for MENTSH appear to be due in part to Akt signaling in a cell-specific manner. Specifically, it was observed that phosphorylated Akt increases in differentiated 3T3 adipocytes, but this was not observed in differentiated L6 myocytes.

These observed effects for MENTSH appear to be due in part to Akt signaling in a cell-specific manner. Specifically, it was observed that phosphorylated Akt increase in differentiated 3T3 adipocytes, but this was not observed in differentiated L6 myocytes (FIG. 7).

Example 9

MENTSH Reduces Weight Gain Only in Mice Fed a High-Fat Diet (HFD)

Figure 8:
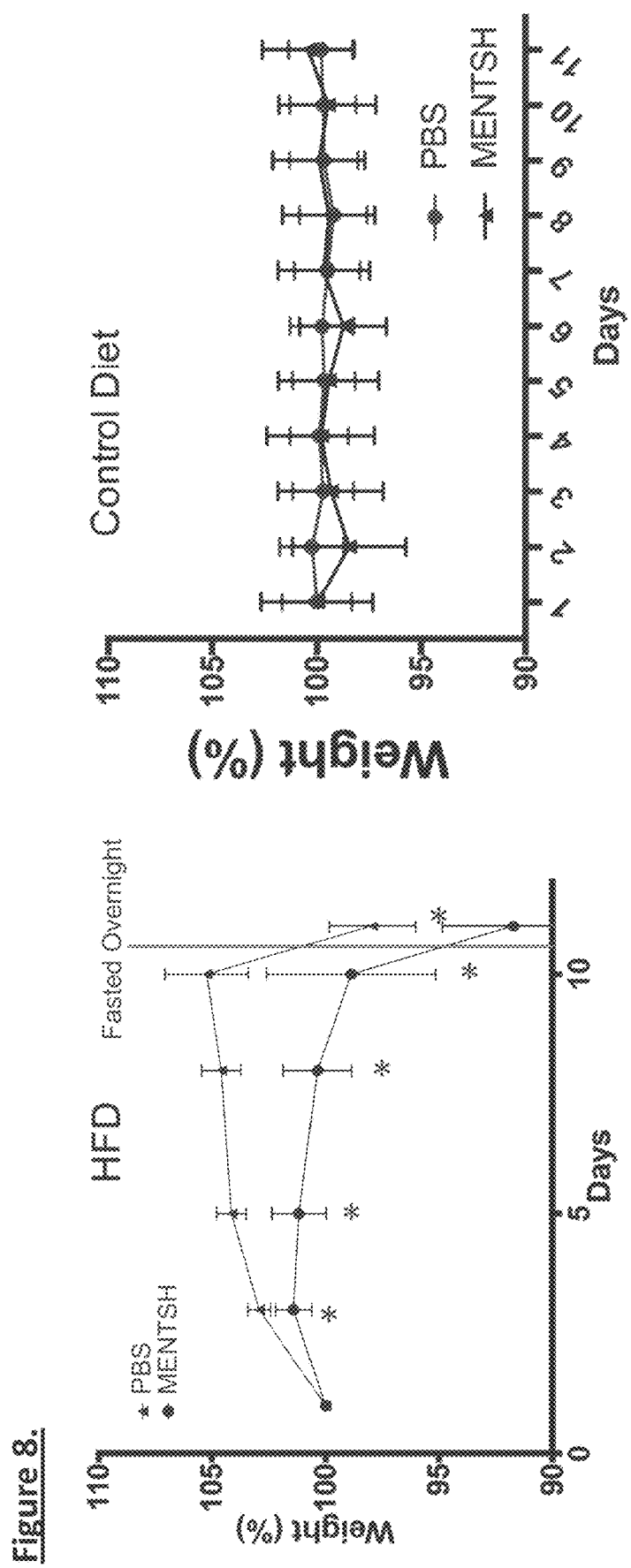
FIG. 8. MENTSH reduces weight gain only in mice fed a high-fat diet (HFD). It was observed that MENTSH most dramatically reduces weight gain in mice fed a high fat diet, thereby implicating anti-obesity effects.

In vivo studies were performed in a 2-Week study of MENTSH administration in mice. Mice treated with twice a day 2.5-mg/kg intraperitoneal injections were placed on a high fat diet (HFD) (60% Fat) or normal diet. Preliminarily, it was observed that MENTSH most dramatically reduces weight gain in mice fed a high fat diet, thereby implicating anti-obesity effects (FIG. 8).

Figure 9:
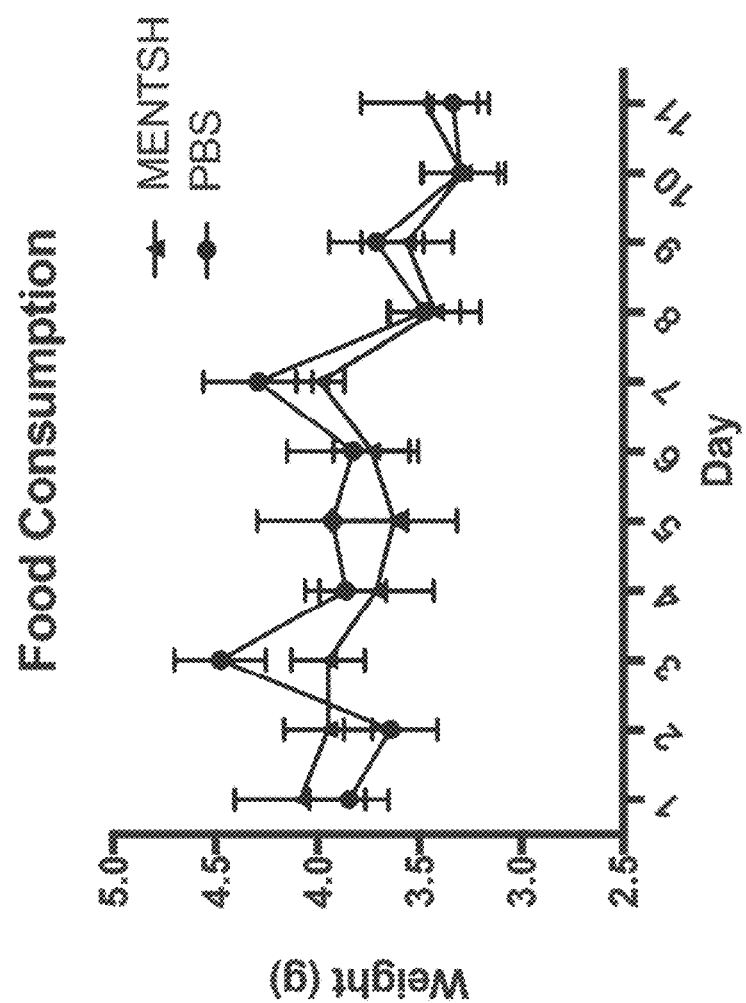
FIG. 9. MENTSH does not change food intake on a high-fat diet or chow diet.
Figure 9:
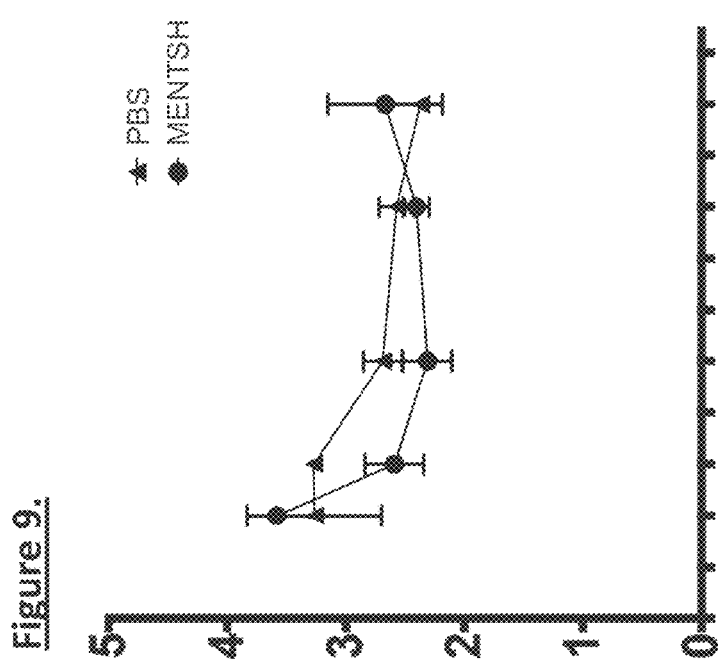
Figure 10:
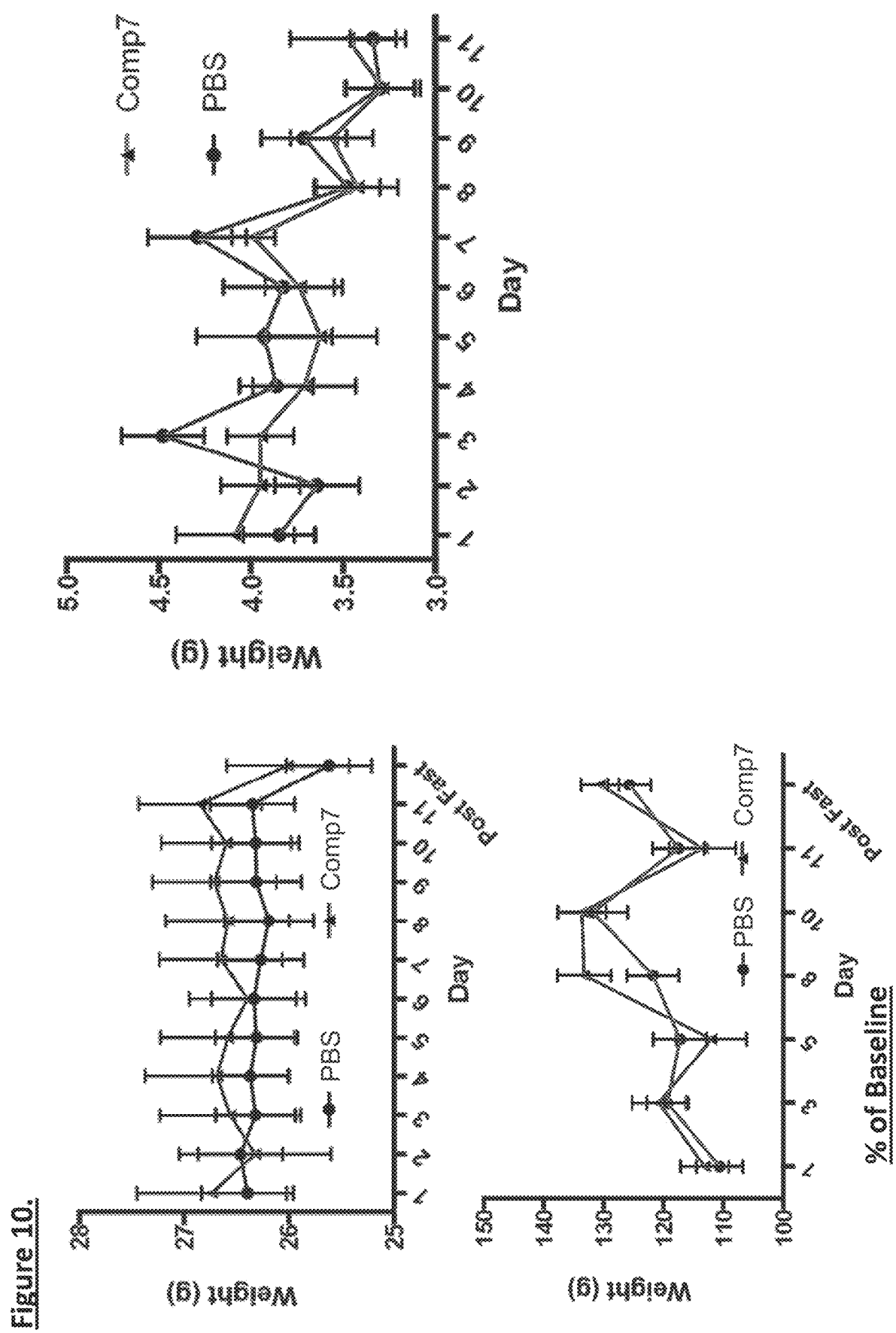
FIG. 10. MENTSH does not change bodyweight and food intake of mice on normal chow.

Importantly, these effects were not due to changes in food intake as MENTSH does not change food intake (FIG. 9). Moreover, MENTSH does not change bodyweight and food intake of mice on normal chow (FIG. 10, also FIGS. 8 and 9).

Example 10

Figure 11:
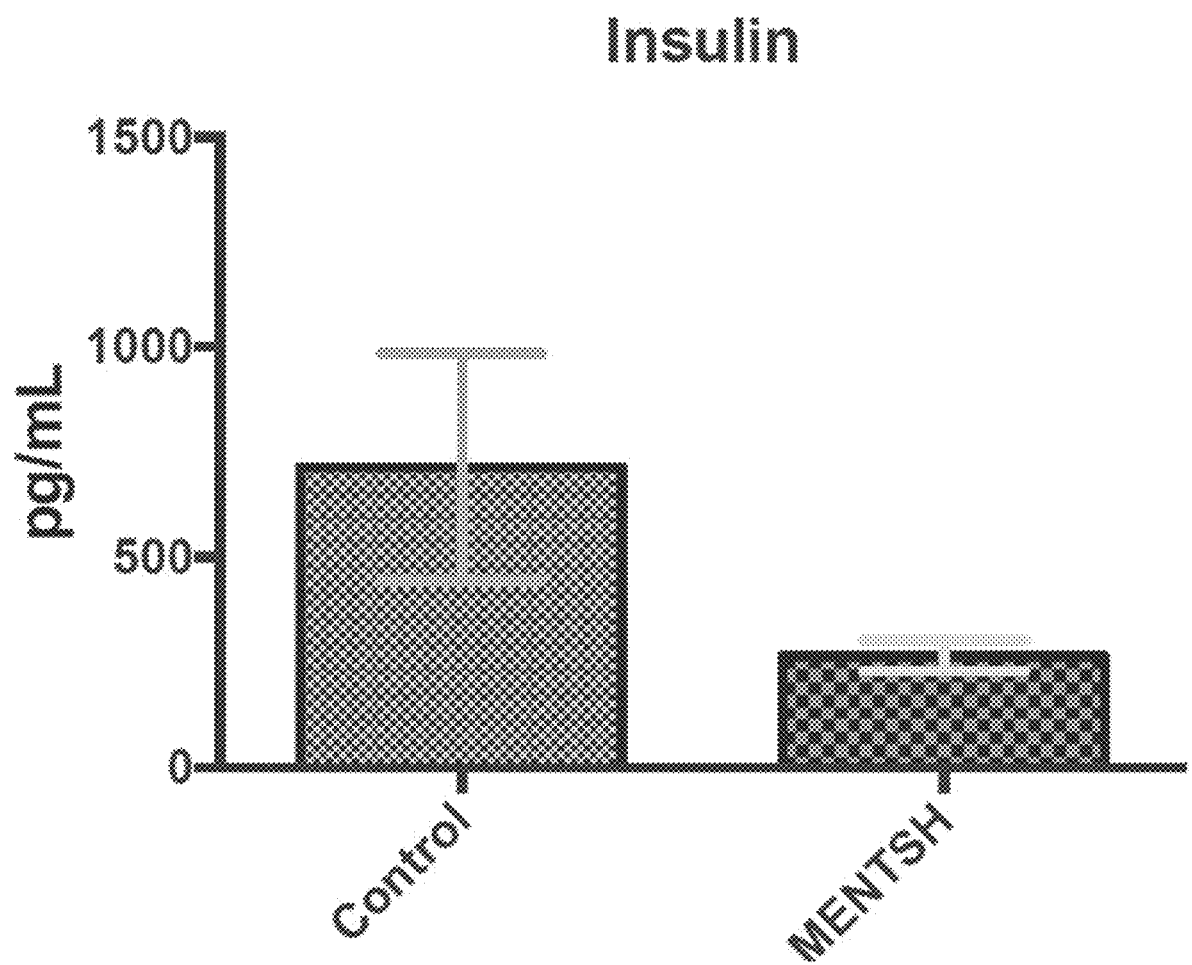
FIG. 11. MENTSH improves insulin sensitivity and insulin levels of mice on a HFD.
Figure 12:
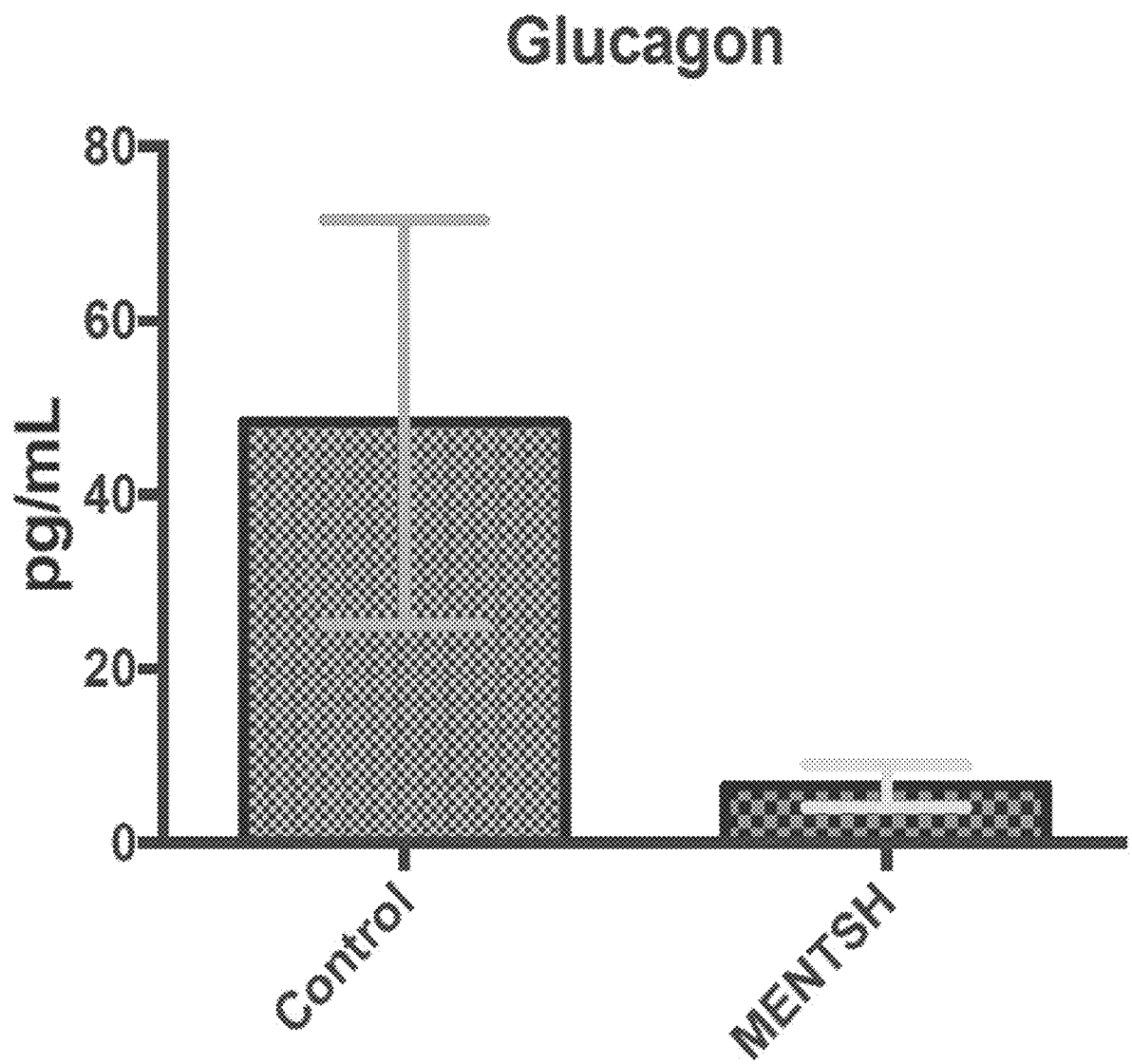
FIG. 12. MENTSH decreases glucagon levels of mice on a HFD.
Figure 13:
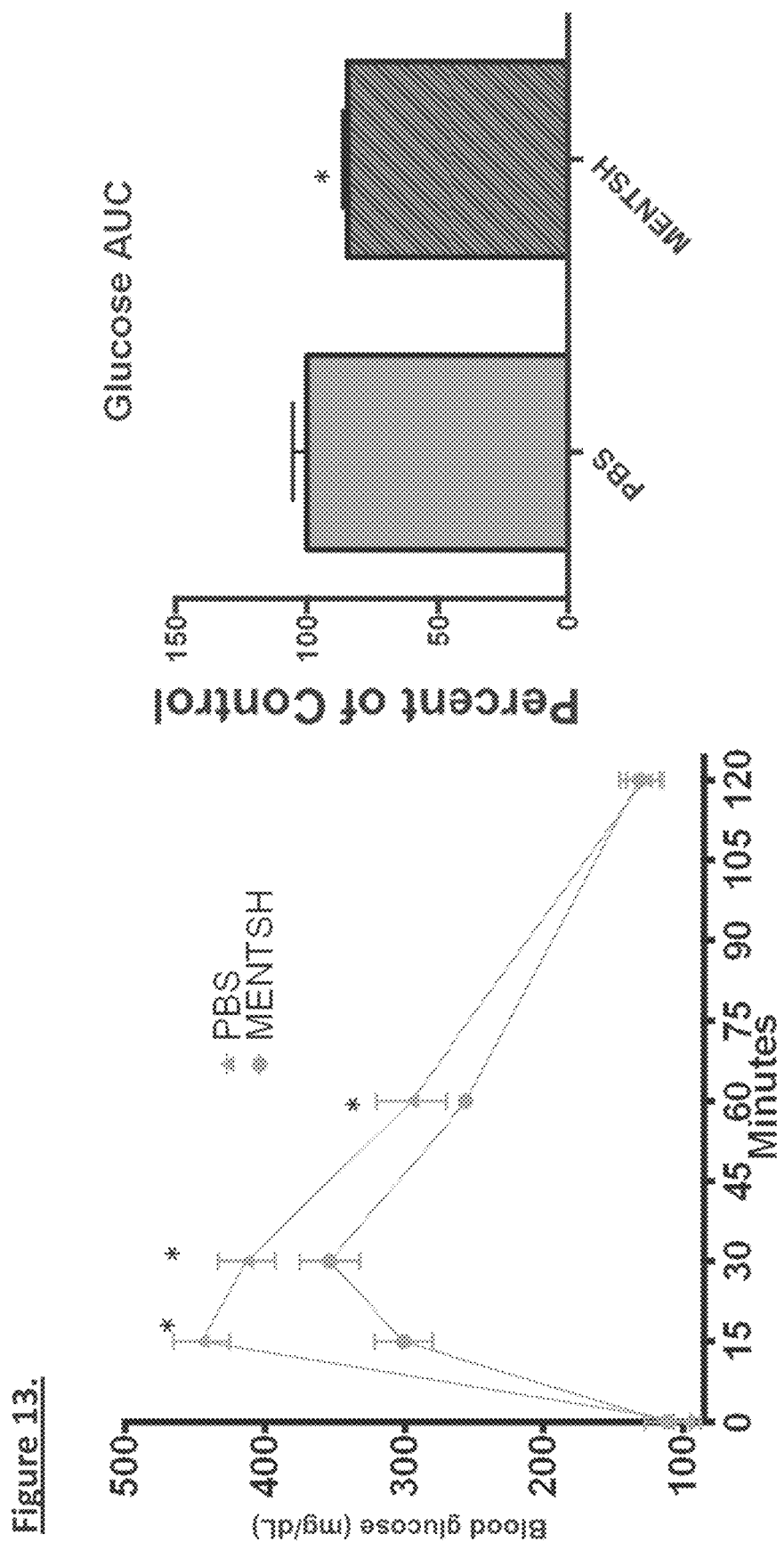
FIG. 13. Improves glucose response on a HFD.

MENTSH Improves Insulin Sensitivity and Insulin Levels, Decreases Glucagon, Improves Glucose Response of Mice on a HFD Importantly, it was observed that insulin sensitivity increased as MENTSH administration decreased insulin levels in animals on HFD compared to controls (FIG. 11). Moreover, MENTSH decreases glucagon levels of mice on a HFD, and improves glucose response (FIG. 12, FIG. 13).

Example 11

Metabolomics of Plasma Suggests Increased Fat Utilization

Figure 14:
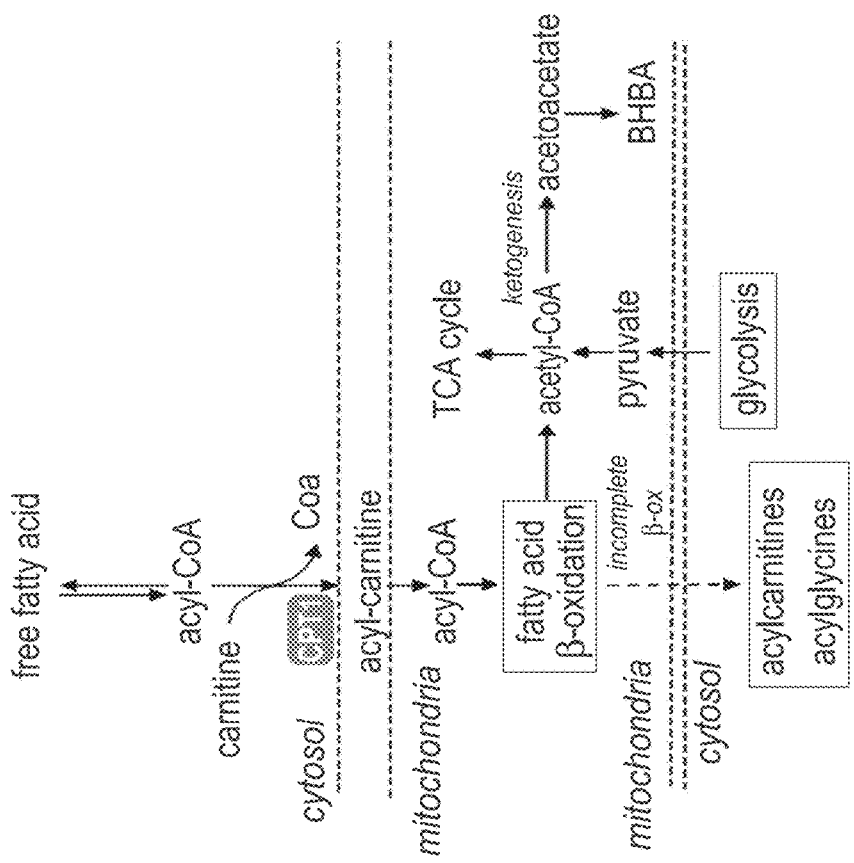
FIG. 14. Metabolomics of plasma suggests increased fat utilization. The decrease in circulating levels of metabolites utilized in lipid usage suggests an increased level of lipid usage within cells.
Figure 15:
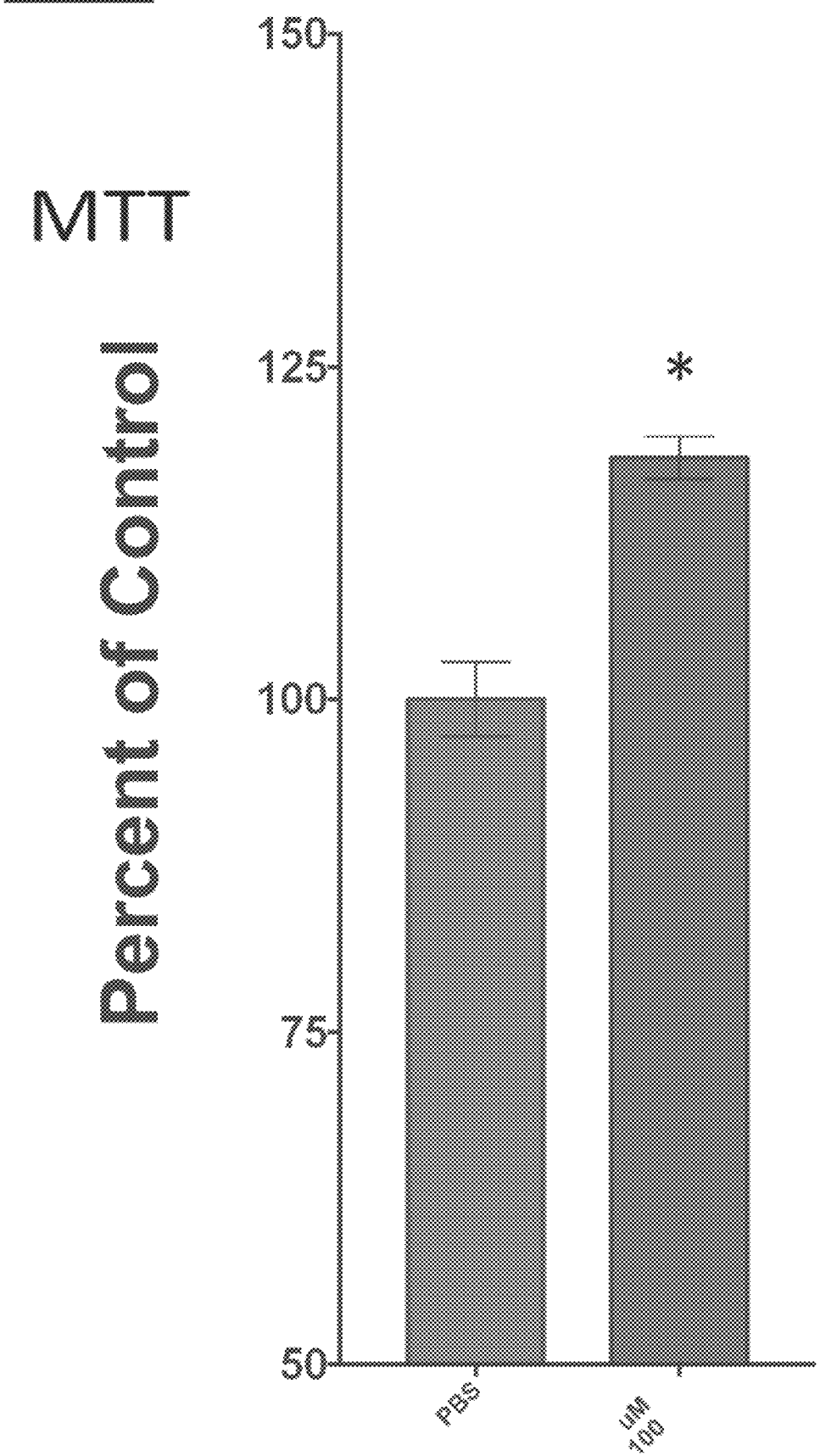
FIG. 15. MENTSH increases bioactivity in 3T3/pre-adipocytes.
Figure 16:
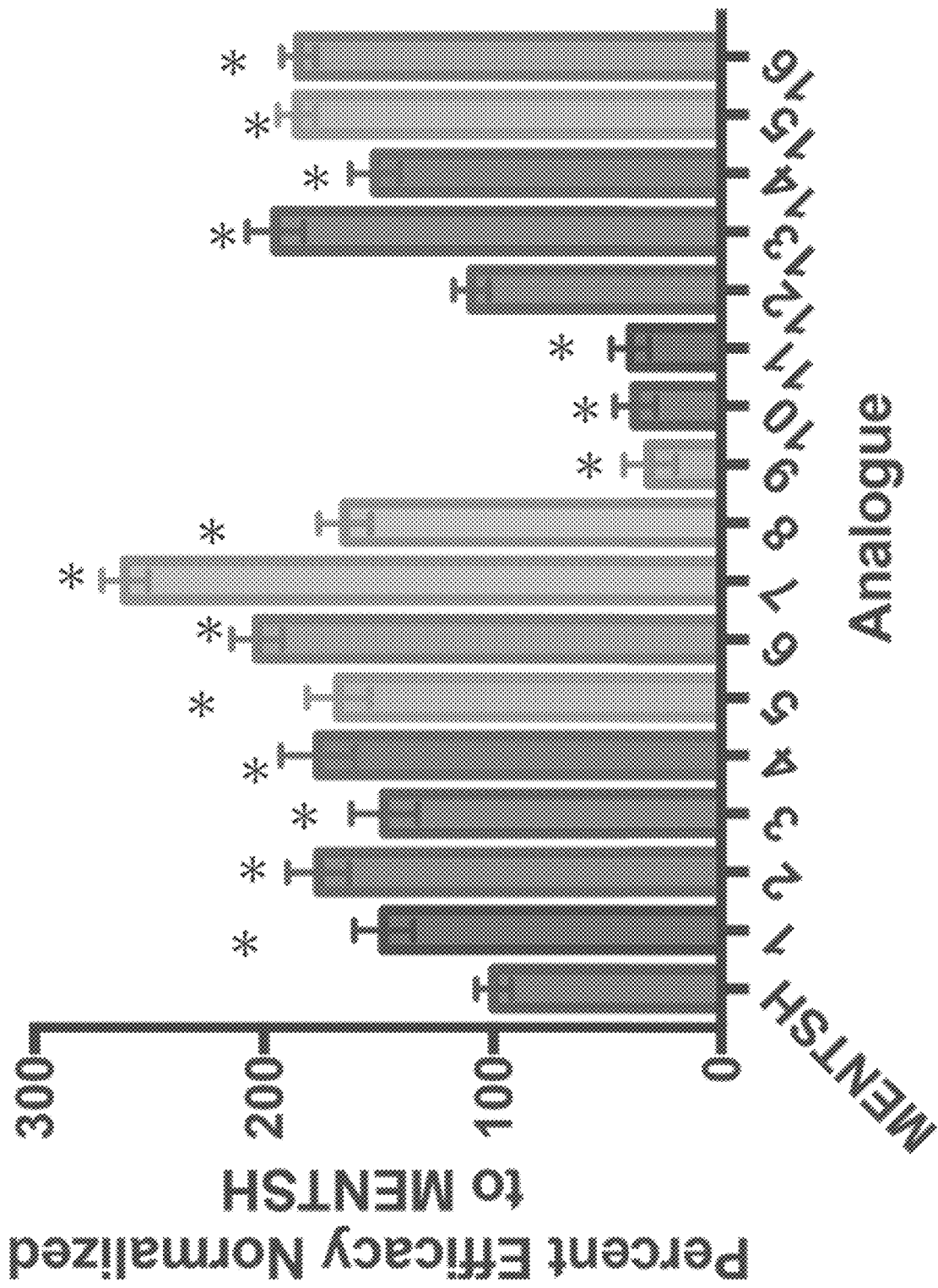
FIG. 16. In Vitro analogue screen in 3T3/pre-adipocytes. Based on MENTSH analogs listed in Table 1. As can be seen, modification can dramatically enhance, and also abrogate MENTSH activity.
Figure 17:
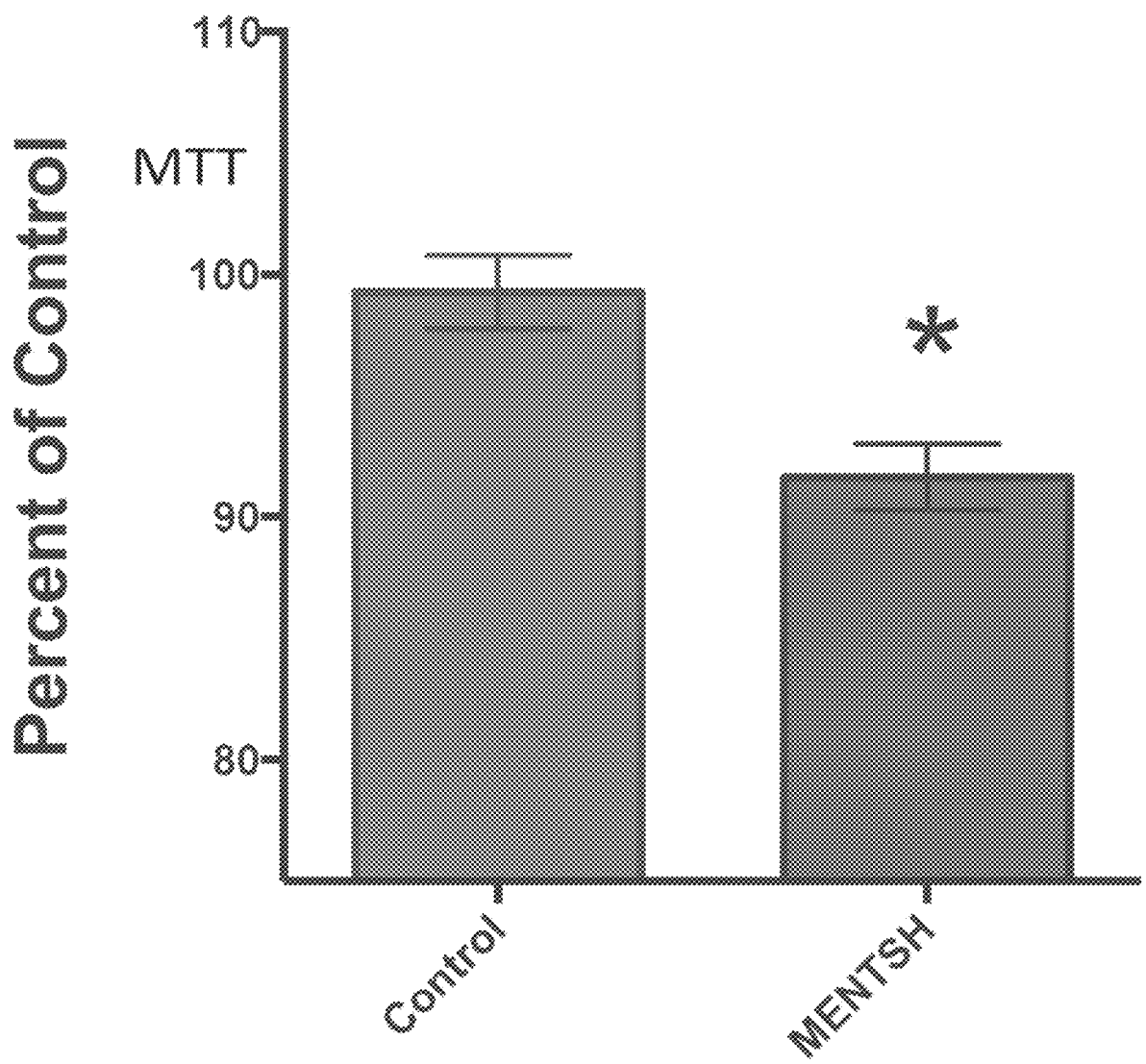
FIG. 17. MENTSH decreases bioactivity in HEK293 cells.
Figure 18:
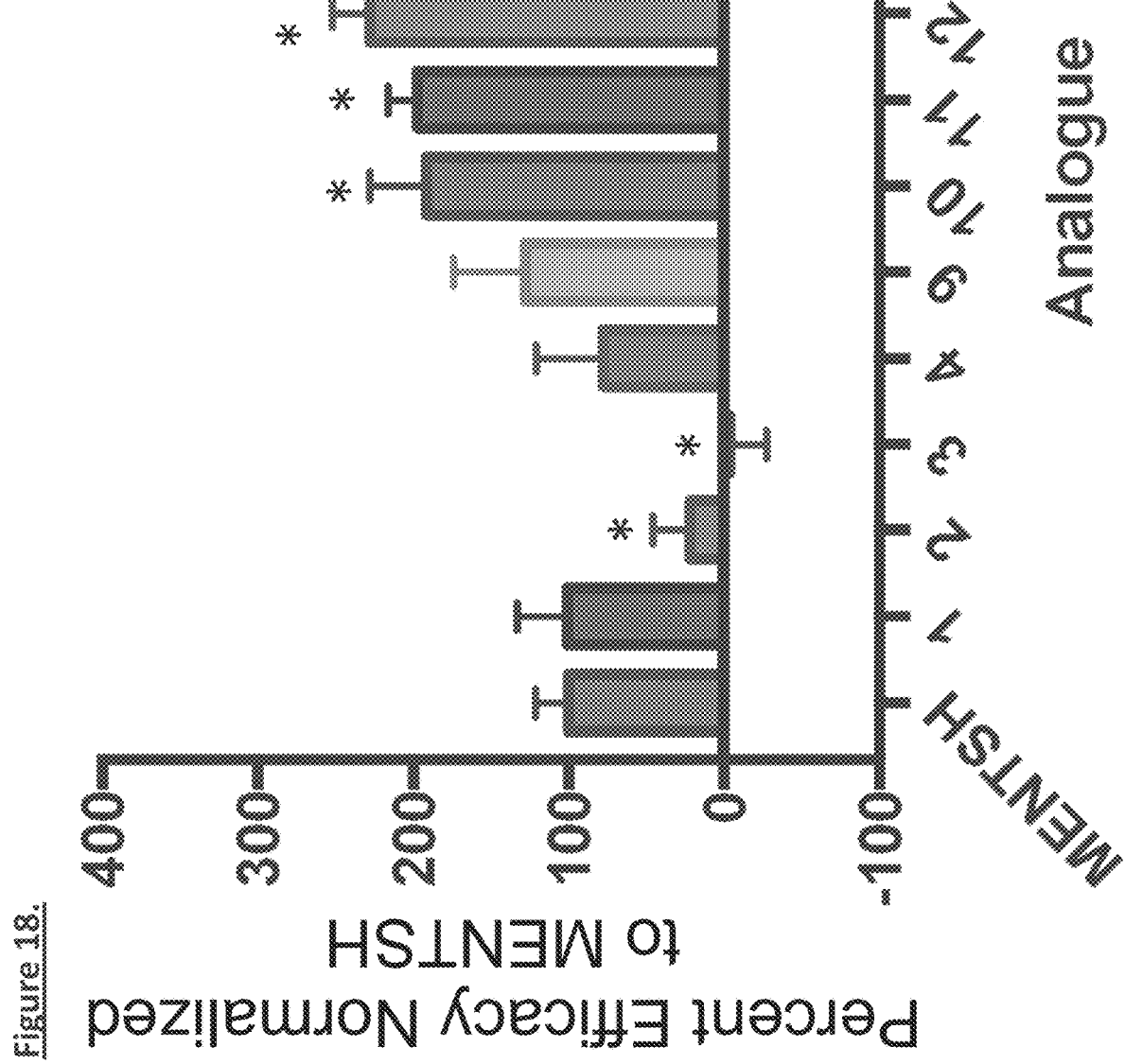
FIG. 18. In Vitro analogue screen.

Metabolomics of plasma suggests increased fat utilization. MENTSH administration in treated mice was correlated with a decrease of fatty acid metabolites, thereby suggesting increased fat utilization within cells (FIG. 14). Via MTT assay, it was observed that MENTSH Increases Bioactivity in 3T3/pre-adipocytes, whereas MENTSH Decreases Bioactivity in HEK293 Cells (FIG. 15, FIG. 17).

Example 12

In Vitro Analogue Screen

Mitochondrial MENTSH peptide can be modified to generate analogs possessing enhanced or abrogated biological activity. Exemplary analogs are shown in Table 1 and testing of such analogs has already identified several lead candidates possessing multiple fold enhancement of activity relative to MENTSH. Interestingly at least some biological effects are cell-specific. In other instances, analogs may possess abrogated activity (FIG. 16, FIG. 18, FIG. 20 and FIG. 21).

Example 13

Figure 19:
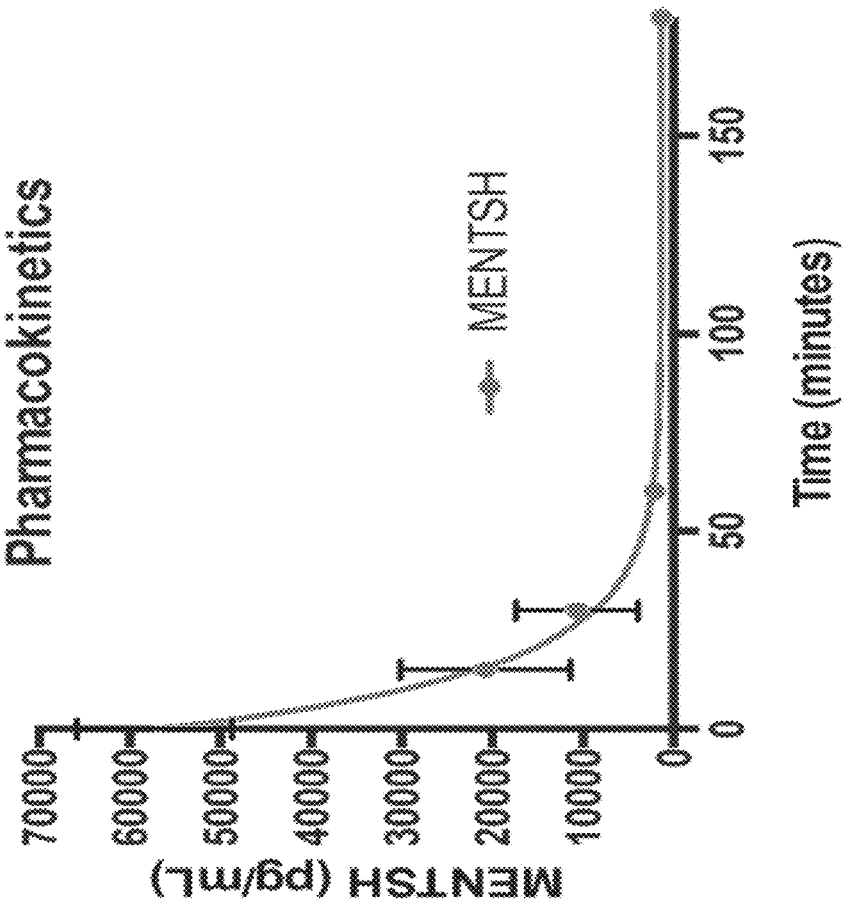
FIG. 19. Detection of MENTSH mRNA and peptide and pharmacokinetics of injected peptide in mice. Northern blot hybridization identified the presence of MENTSH transcript in mitochondrial mRNA. An ELISA assay developed by the Inventors for detection of MENTSH revealed a relatively short persistence (e.g., ~1 hr) of MENTSH.
Figure 19:
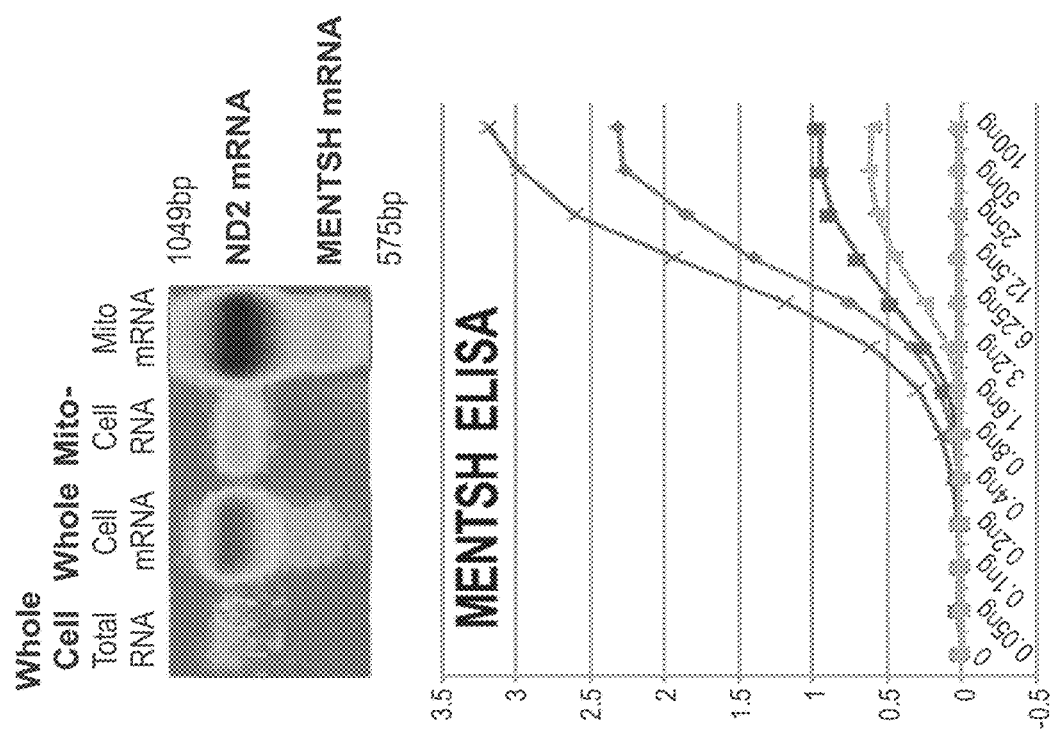
Figure 20:
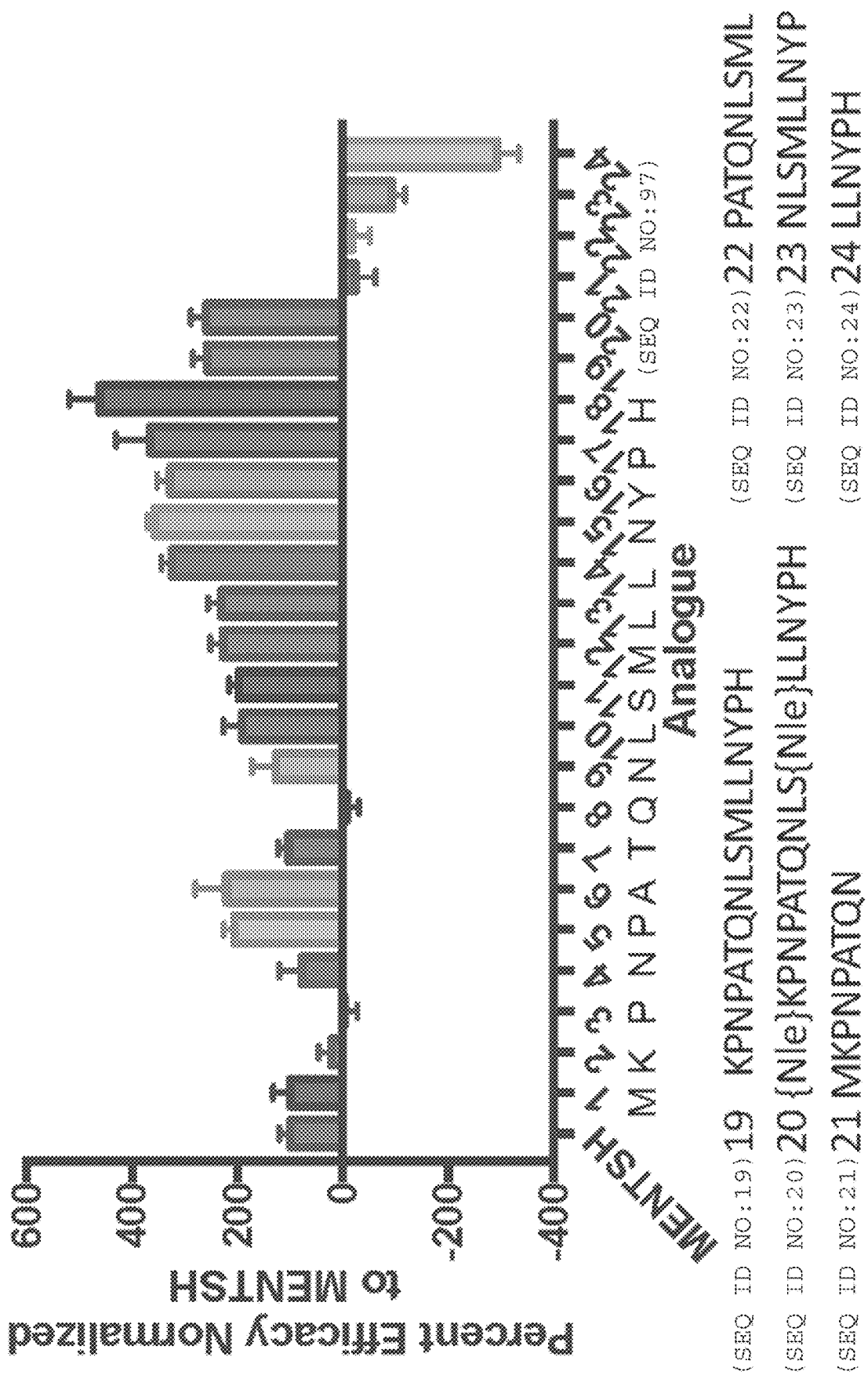
FIG. 20. In Vitro screening of analogues to SEQ ID NO:97 in 3T3/pre-adipocytes. Analogues include SEQ ID NO:19 to SEQ ID NO:24.
Figure 21:
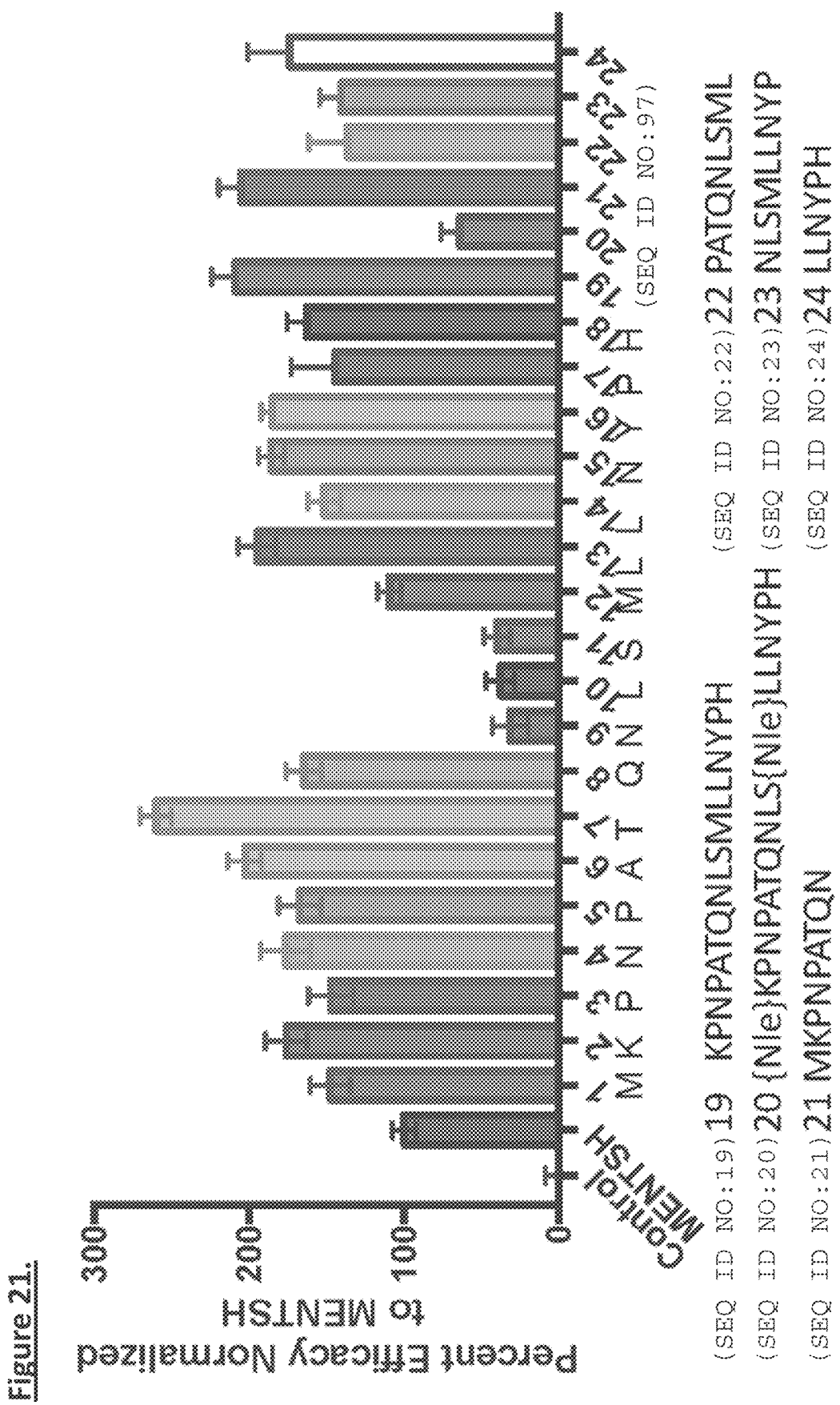
FIG. 21. In Vitro screening of analogues to SEQ ID NO:97 in HEK293 cells. Analogues include SEQ ID NO:19 to SEQ ID NO: 24.

Detection of MENTSH mRNA and Peptide and Pharmacokinetics of Injected Peptide in Mice Northern blot hybridization identified the presence of MENTSH transcript in mitochondrial mRNA (FIG. 19). Further, the Inventors developed an ELISA assay for detection of MENTSH. Pharmacokinetics revealed relatively short persistence (e.g., ~1 hr) of MENTSH (FIG. 19). Increasing persistent bioavailability of MENTSH by analogs, or other artificial modifications may further improve biological effects for therapeutic use.

Example 14

Cholesterol, Dyslipdemia

Figure 22:
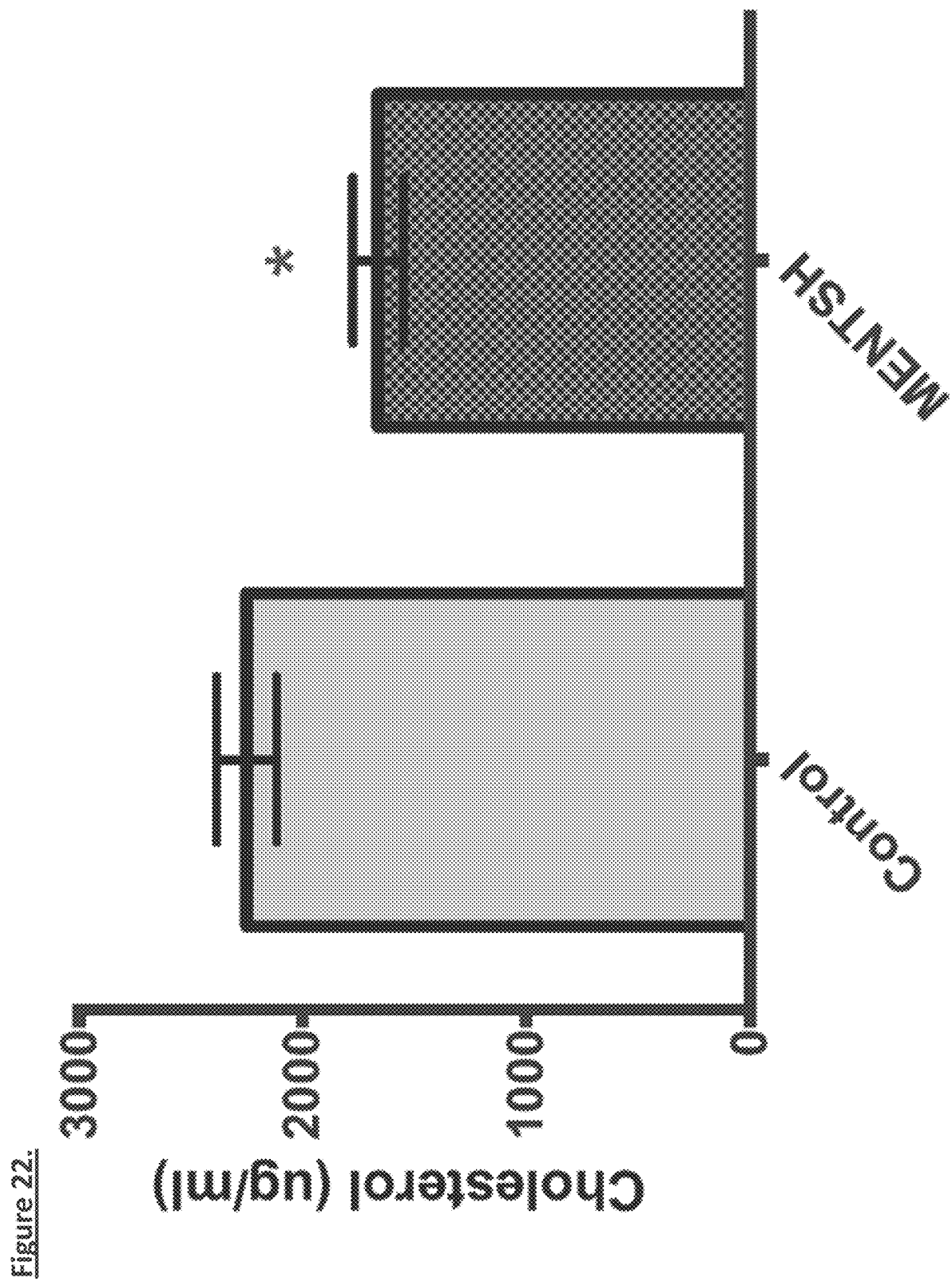
FIG. 22. Cholesterol levels in HepG2 cells. In a human, liver cell line, treatment with MENTSH reduced total cellular cholesterol levels within 48 hours of treatment (10 µM).
Figure 23:
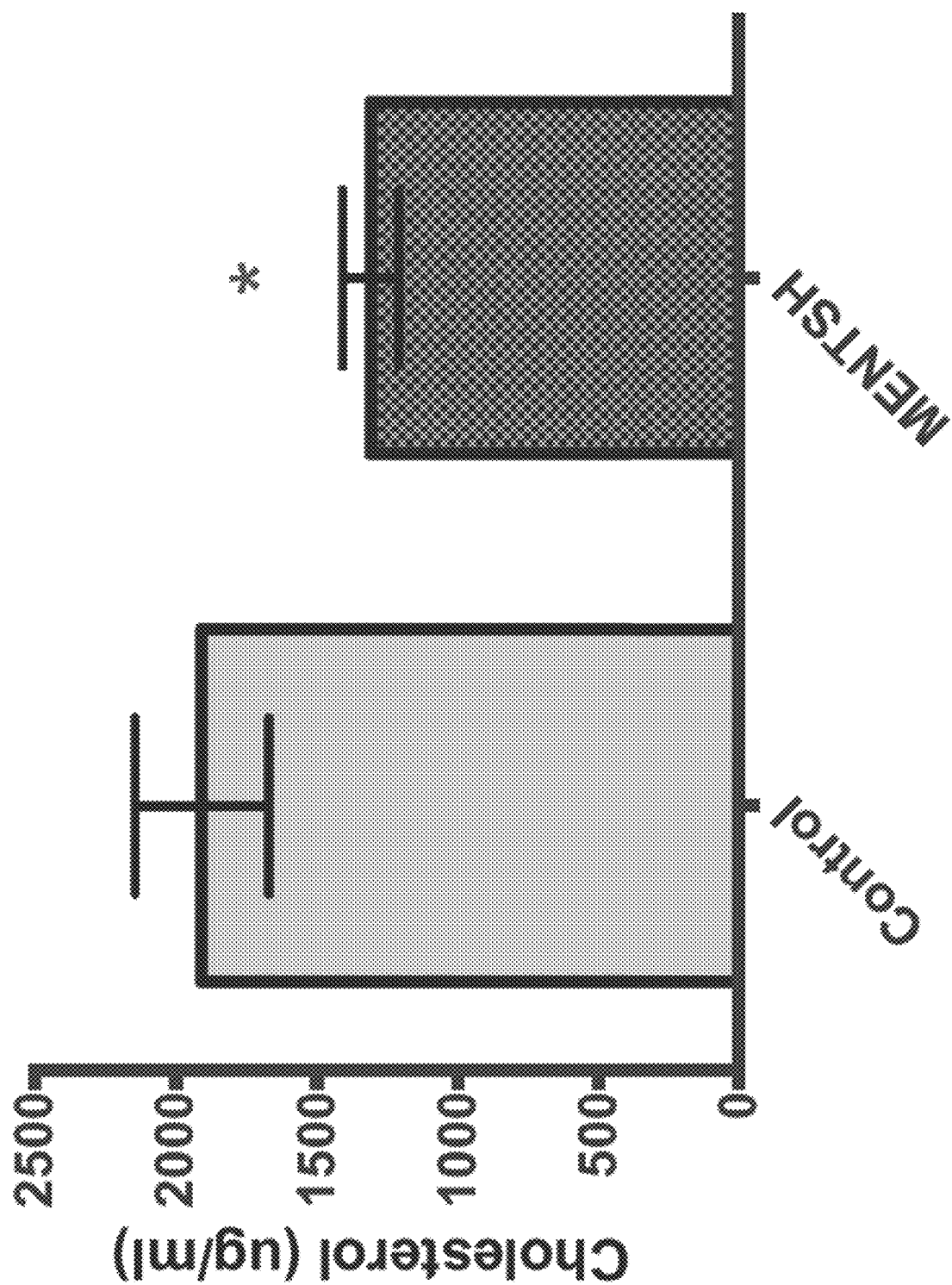
FIG. 23. Cholesterol levels in obese mice. Cholesterol levels were reduced within 72 hours of MENTSH treatment (2.5 mg/kg bid) in mice with diet-induced obesity.

The Inventors have further discovered that MENTSH treatment in cell culture model, MENTSH treated human HepG2 liver cells also show a decrease in cholesterol (FIG. 22). These results were confirmed in animal studies, wherein MENTSH treated obese mice experience reduce cholesterol levels in 72 hours, suggesting that MENTSH may be a therapeutic for hypercholesterolemia and related diseases (FIG. 23).

Example 15

Analog Screen

Figure 24:
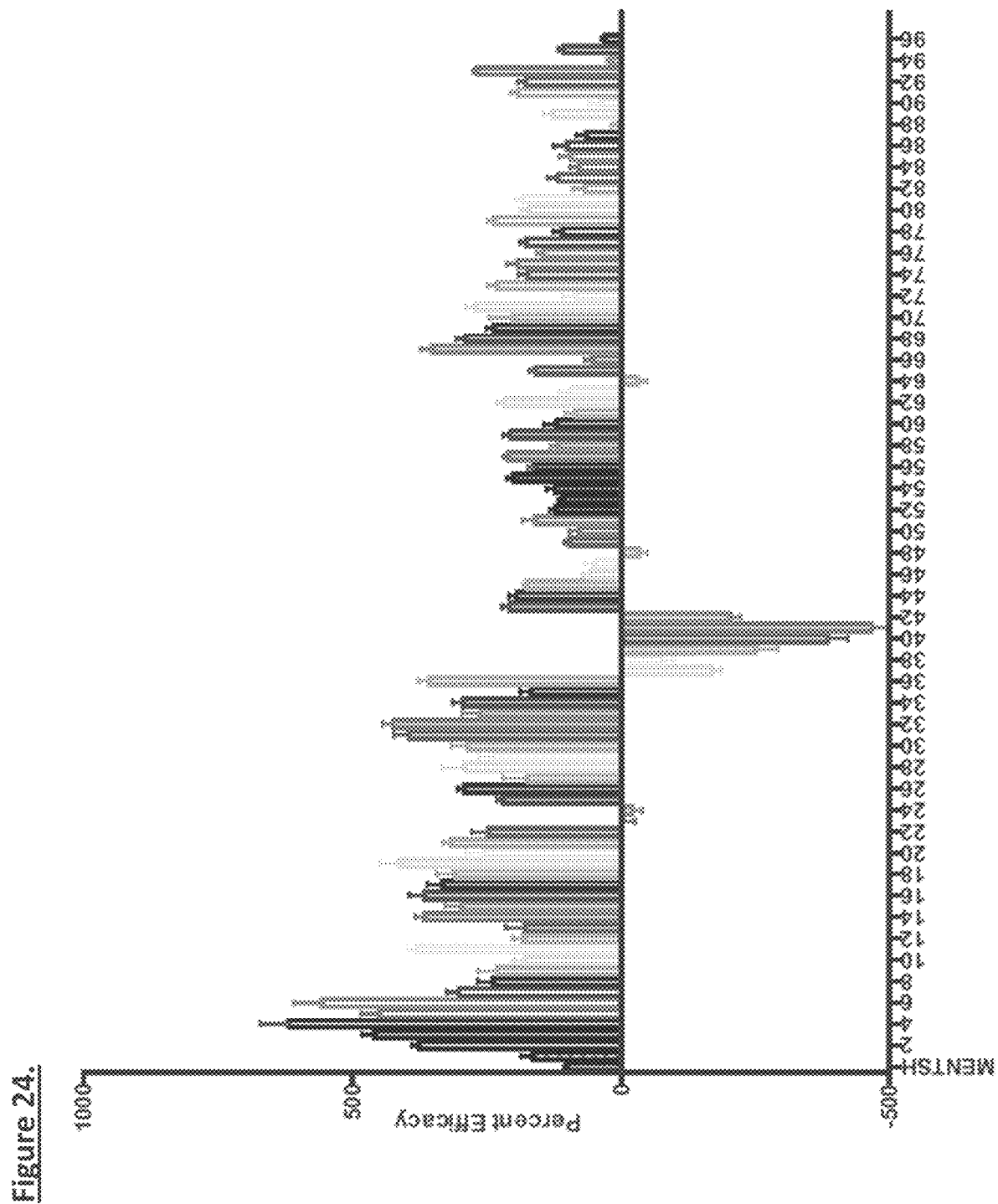
FIG. 24. In Vitro analogue screen in murine adipocyte cell line. Treatment of MENTSH analogues to a murine adipocyte cell line found many improved analogues with over 500% efficacy as well as several novel MENTSH antagonists that caused an opposite effect on adipocytes.

The Inventors have completed a screen of 96 different MENTSH analogs constituting SEQ ID NO: 1 to SEQ ID NO: 96 in Table 1 for bioactivity. The Inventors have several that are over 500% more effective than MENTSH (FIG. 24).

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are mitochondrial peptides and methods of preparing and/or isolating said peptides, uses of said peptides in the treatment of diseases and/or conditions that relate to the teachings of the invention, further including techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A composition comprising:
a peptide comprising the amino acid sequence with 70% or more percent identity to SEQ ID NO:97, wherein the peptide comprises the amino acid sequence of any one of SEQ ID NOs: 1-20, 25-36, 43-47, 49-63, 65-87, 89, 91-93, and 95, or wherein the peptide is 16, 17, 19, 20, 21, or 22 amino acids in length.

2. A composition comprising:
a peptide comprising the amino acid sequence with 70% or more percent identity to SEQ ID NO: 97, wherein the peptide 16 amino acids in length.

3. The composition of claim 1, wherein the peptide consists of the amino acid sequence of any one of SEQ ID NOs: 1-20, 25-36, 43-47, 49-63, 65-87, 89, 91-93, and 95.

4. The composition of claim 1, wherein the peptide contains a negatively charged amino acid as a substitute for threonine-7, serine-11, tyrosine-16, or a combination thereof of, wherein the positions are relative to SEQ ID NO:97, or wherein the peptide contains a negatively charged amino acid as a substitute for serine-11 and tyrosine-16, wherein the positions are relative to SEQ ID NO:97.

5. A composition comprising:
a peptide comprising the amino acid sequence with 70% or more percent identity to SEQ ID NO: 97, wherein the peptide is 16 amino acids in length, wherein the peptide contains a negatively charged amino acid as a substitute for serine-11 and tyrosine-16, wherein the positions are relative to SEQ ID NO:97, and wherein at least one of the negatively charged amino acids is aspartic acid.

6. The composition of claim 5, wherein each of the negatively charged amino acids is aspartic acid.

7. The composition of claim 2, wherein the peptide comprises the amino acid sequence with 80% or more percent identity to SEQ ID NO:97.

8. The composition of claim 2, wherein the peptide comprises the amino acid sequence with 85% or more percent identity to SEQ ID NO:97.

9. The composition of claim 1, wherein the peptide comprises a post-translational or artificial modification.

10. The composition of claim 9, wherein the artificial modification comprises pegylation, fatty-acid conjugation, polypeptide extension, Immunoglobulin G fragment crystallizable region (IgG-Fc), carnitine palmitoyltransferase (CPT), human serum albumin (HSA), elastin-like polypeptide (ELP), transferrin, or albumin modification.

* * * * *

SEQUENCE LISTING

Sequence total quantity: 98

```
SEQ ID NO: 1           moltype = AA  length = 18
FEATURE                Location/Qualifiers
REGION                 1..18
                       note = peptide
source                 1..18
                       mol_type = protein
                       organism = synthetic construct
SEQUENCE: 1
AKPNPATQNL SMLLNYPH                                                    18

SEQ ID NO: 2           moltype = AA  length = 18
FEATURE                Location/Qualifiers
REGION                 1..18
                       note = peptide
source                 1..18
                       mol_type = protein
                       organism = synthetic construct
SEQUENCE: 2
MAPNPATQNL SMLLNYPH                                                    18

SEQ ID NO: 3           moltype = AA  length = 18
FEATURE                Location/Qualifiers
REGION                 1..18
                       note = peptide
source                 1..18
                       mol_type = protein
                       organism = synthetic construct
SEQUENCE: 3
MKANPATQNL SMLLNYPH                                                    18

SEQ ID NO: 4           moltype = AA  length = 18
FEATURE                Location/Qualifiers
REGION                 1..18
                       note = peptide
source                 1..18
                       mol_type = protein
                       organism = synthetic construct
SEQUENCE: 4
MKPAPATQNL SMLLNYPH                                                    18

SEQ ID NO: 5           moltype = AA  length = 18
FEATURE                Location/Qualifiers
REGION                 1..18
                       note = peptide
source                 1..18
                       mol_type = protein
                       organism = synthetic construct
SEQUENCE: 5
MKPNAATQNL SMLLNYPH                                                    18

SEQ ID NO: 6           moltype = AA  length = 18
FEATURE                Location/Qualifiers
REGION                 1..18
                       note = peptide
source                 1..18
                       mol_type = protein
                       organism = synthetic construct
SEQUENCE: 6
MKPNPATQNL SMLLNYPH                                                    18

SEQ ID NO: 7           moltype = AA  length = 18
FEATURE                Location/Qualifiers
REGION                 1..18
                       note = peptide
source                 1..18
                       mol_type = protein
                       organism = synthetic construct
SEQUENCE: 7
MKPNPAAQNL SMLLNYPH                                                    18

SEQ ID NO: 8           moltype = AA  length = 18
FEATURE                Location/Qualifiers
REGION                 1..18
                       note = peptide
source                 1..18
                       mol_type = protein
                       organism = synthetic construct
```

```
SEQUENCE: 8
MKPNPATANL SMLLNYPH                                                      18

SEQ ID NO: 9          moltype = AA  length = 18
FEATURE               Location/Qualifiers
REGION                1..18
                      note = peptide
source                1..18
                      mol_type = protein
                      organism = synthetic construct
SEQUENCE: 9
MKPNPATQAL SMLLNYPH                                                      18

SEQ ID NO: 10         moltype = AA  length = 18
FEATURE               Location/Qualifiers
REGION                1..18
                      note = peptide
source                1..18
                      mol_type = protein
                      organism = synthetic construct
SEQUENCE: 10
MKPNPATQNA SMLLNYPH                                                      18

SEQ ID NO: 11         moltype = AA  length = 18
FEATURE               Location/Qualifiers
REGION                1..18
                      note = peptide
source                1..18
                      mol_type = protein
                      organism = synthetic construct
SEQUENCE: 11
MKPNPATQNL AMLLNYPH                                                      18

SEQ ID NO: 12         moltype = AA  length = 18
FEATURE               Location/Qualifiers
REGION                1..18
                      note = peptide
source                1..18
                      mol_type = protein
                      organism = synthetic construct
SEQUENCE: 12
MKPNPATQNL SALLNYPH                                                      18

SEQ ID NO: 13         moltype = AA  length = 18
FEATURE               Location/Qualifiers
REGION                1..18
                      note = peptide
source                1..18
                      mol_type = protein
                      organism = synthetic construct
SEQUENCE: 13
MKPNPATQNL SMALNYPH                                                      18

SEQ ID NO: 14         moltype = AA  length = 18
FEATURE               Location/Qualifiers
REGION                1..18
                      note = peptide
source                1..18
                      mol_type = protein
                      organism = synthetic construct
SEQUENCE: 14
MKPNPATQNL SMLANYPH                                                      18

SEQ ID NO: 15         moltype = AA  length = 18
FEATURE               Location/Qualifiers
REGION                1..18
                      note = peptide
source                1..18
                      mol_type = protein
                      organism = synthetic construct
SEQUENCE: 15
MKPNPATQNL SMLLAYPH                                                      18

SEQ ID NO: 16         moltype = AA  length = 18
FEATURE               Location/Qualifiers
REGION                1..18
                      note = peptide
source                1..18
                      mol_type = protein
```

```
                                              organism = synthetic construct
SEQUENCE: 16
MKPNPATQNL SMLLNAPH                                                               18

SEQ ID NO: 17              moltype = AA   length = 18
FEATURE                    Location/Qualifiers
REGION                     1..18
                           note = peptide
source                     1..18
                           mol_type = protein
                           organism = synthetic construct
SEQUENCE: 17
MKPNPATQNL SMLLNYAH                                                               18

SEQ ID NO: 18              moltype = AA   length = 18
FEATURE                    Location/Qualifiers
REGION                     1..18
                           note = peptide
source                     1..18
                           mol_type = protein
                           organism = synthetic construct
SEQUENCE: 18
MKPNPATQNL SMLLNYPA                                                               18

SEQ ID NO: 19              moltype = AA   length = 17
FEATURE                    Location/Qualifiers
REGION                     1..17
                           note = peptide
source                     1..17
                           mol_type = protein
                           organism = synthetic construct
SEQUENCE: 19
KPNPATQNLS MLLNYPH                                                                17

SEQ ID NO: 20              moltype = AA   length = 22
FEATURE                    Location/Qualifiers
REGION                     1..22
                           note = peptide
source                     1..22
                           mol_type = protein
                           organism = synthetic construct
SEQUENCE: 20
NLEKPNPATQ NLSNLELLNY PH                                                          22

SEQ ID NO: 21              moltype = AA   length = 9
FEATURE                    Location/Qualifiers
REGION                     1..9
                           note = peptide
source                     1..9
                           mol_type = protein
                           organism = synthetic construct
SEQUENCE: 21
MKPNPATQN                                                                          9

SEQ ID NO: 22              moltype = AA   length = 9
FEATURE                    Location/Qualifiers
REGION                     1..9
                           note = peptide
source                     1..9
                           mol_type = protein
                           organism = synthetic construct
SEQUENCE: 22
PATQNLSML                                                                          9

SEQ ID NO: 23              moltype = AA   length = 9
FEATURE                    Location/Qualifiers
REGION                     1..9
                           note = peptide
source                     1..9
                           mol_type = protein
                           organism = synthetic construct
SEQUENCE: 23
NLSMLLNYP                                                                          9

SEQ ID NO: 24              moltype = AA   length = 6
FEATURE                    Location/Qualifiers
REGION                     1..6
                           note = peptide
source                     1..6
```

```
                        mol_type = protein
                        organism = synthetic construct
SEQUENCE: 24
LLNYPH                                                                    6

SEQ ID NO: 25           moltype = AA  length = 18
FEATURE                 Location/Qualifiers
REGION                  1..18
                        note = peptide
source                  1..18
                        mol_type = protein
                        organism = synthetic construct
SEQUENCE: 25
MKANAATQNL SMLLNYAH                                                      18

SEQ ID NO: 26           moltype = AA  length = 18
FEATURE                 Location/Qualifiers
REGION                  1..18
                        note = peptide
source                  1..18
                        mol_type = protein
                        organism = synthetic construct
SEQUENCE: 26
MKGNGATQNL SMLLNYGH                                                      18

SEQ ID NO: 27           moltype = AA  length = 18
FEATURE                 Location/Qualifiers
REGION                  1..18
                        note = peptide
source                  1..18
                        mol_type = protein
                        organism = synthetic construct
SEQUENCE: 27
MKANAATQNL SMLLNYPH                                                      18

SEQ ID NO: 28           moltype = AA  length = 18
FEATURE                 Location/Qualifiers
REGION                  1..18
                        note = peptide
source                  1..18
                        mol_type = protein
                        organism = synthetic construct
SEQUENCE: 28
MKPNAATQNL SMLLNYAH                                                      18

SEQ ID NO: 29           moltype = AA  length = 18
FEATURE                 Location/Qualifiers
REGION                  1..18
                        note = peptide
source                  1..18
                        mol_type = protein
                        organism = synthetic construct
SEQUENCE: 29
MKANPATQNL SMLLNYAH                                                      18

SEQ ID NO: 30           moltype = AA  length = 18
FEATURE                 Location/Qualifiers
REGION                  1..18
                        note = peptide
source                  1..18
                        mol_type = protein
                        organism = synthetic construct
SEQUENCE: 30
MKPNPADQNL DMLLNDPH                                                      18

SEQ ID NO: 31           moltype = AA  length = 18
FEATURE                 Location/Qualifiers
REGION                  1..18
                        note = peptide
source                  1..18
                        mol_type = protein
                        organism = synthetic construct
SEQUENCE: 31
MKPNPADQNL DMLLNYPH                                                      18

SEQ ID NO: 32           moltype = AA  length = 18
FEATURE                 Location/Qualifiers
REGION                  1..18
                        note = peptide
```

```
source                          1..18
                                mol_type = protein
                                organism = synthetic construct
SEQUENCE: 32
MKPNPATQNL DMLLNDPH                                                    18

SEQ ID NO: 33                   moltype = AA   length = 18
FEATURE                         Location/Qualifiers
REGION                          1..18
                                note = peptide
source                          1..18
                                mol_type = protein
                                organism = synthetic construct
SEQUENCE: 33
MKPNPADQNL SMLLNDPH                                                    18

SEQ ID NO: 34                   moltype = AA   length = 18
FEATURE                         Location/Qualifiers
REGION                          1..18
                                note = peptide
source                          1..18
                                mol_type = protein
                                organism = synthetic construct
SEQUENCE: 34
MKPNPADQNL SMLLNYPH                                                    18

SEQ ID NO: 35                   moltype = AA   length = 18
FEATURE                         Location/Qualifiers
REGION                          1..18
                                note = peptide
source                          1..18
                                mol_type = protein
                                organism = synthetic construct
SEQUENCE: 35
MKPNPATQNL DMLLNYPH                                                    18

SEQ ID NO: 36                   moltype = AA   length = 18
FEATURE                         Location/Qualifiers
REGION                          1..18
                                note = peptide
source                          1..18
                                mol_type = protein
                                organism = synthetic construct
SEQUENCE: 36
MKPNPATQNL SMLLNDPH                                                    18

SEQ ID NO: 37                   moltype = AA   length = 18
FEATURE                         Location/Qualifiers
REGION                          1..18
                                note = peptide
source                          1..18
                                mol_type = protein
                                organism = synthetic construct
SEQUENCE: 37
MKPNPAGQNL GMLLNGPH                                                    18

SEQ ID NO: 38                   moltype = AA   length = 18
FEATURE                         Location/Qualifiers
REGION                          1..18
                                note = peptide
source                          1..18
                                mol_type = protein
                                organism = synthetic construct
SEQUENCE: 38
MKPNPAGQNL GMLLNYPH                                                    18

SEQ ID NO: 39                   moltype = AA   length = 18
FEATURE                         Location/Qualifiers
REGION                          1..18
                                note = peptide
source                          1..18
                                mol_type = protein
                                organism = synthetic construct
SEQUENCE: 39
MKPNPATQNL GMLLNGPH                                                    18

SEQ ID NO: 40                   moltype = AA   length = 18
FEATURE                         Location/Qualifiers
REGION                          1..18
```

```
                        note = peptide
source                  1..18
                        mol_type = protein
                        organism = synthetic construct
SEQUENCE: 40
MKPNPAGQNL SMLLNGPH                                                 18

SEQ ID NO: 41           moltype = AA  length = 18
FEATURE                 Location/Qualifiers
REGION                  1..18
                        note = peptide
source                  1..18
                        mol_type = protein
                        organism = synthetic construct
SEQUENCE: 41
MKPNPAGQNL SMLLNYPH                                                 18

SEQ ID NO: 42           moltype = AA  length = 18
FEATURE                 Location/Qualifiers
REGION                  1..18
                        note = peptide
source                  1..18
                        mol_type = protein
                        organism = synthetic construct
SEQUENCE: 42
MKPNPATQNL GMLLNYPH                                                 18

SEQ ID NO: 43           moltype = AA  length = 18
FEATURE                 Location/Qualifiers
REGION                  1..18
                        note = peptide
source                  1..18
                        mol_type = protein
                        organism = synthetic construct
SEQUENCE: 43
MKPNPATQNL SMLLNGPH                                                 18

SEQ ID NO: 44           moltype = AA  length = 19
FEATURE                 Location/Qualifiers
REGION                  1..19
                        note = peptide
source                  1..19
                        mol_type = protein
                        organism = synthetic construct
SEQUENCE: 44
EMKPNPSTQN TSMTTNQPH                                                19

SEQ ID NO: 45           moltype = AA  length = 18
FEATURE                 Location/Qualifiers
REGION                  1..18
                        note = peptide
source                  1..18
                        mol_type = protein
                        organism = synthetic construct
SEQUENCE: 45
MKPNPSTQNT SMTTNYPH                                                 18

SEQ ID NO: 46           moltype = AA  length = 18
FEATURE                 Location/Qualifiers
REGION                  1..18
                        note = peptide
source                  1..18
                        mol_type = protein
                        organism = synthetic construct
SEQUENCE: 46
MKPNPSTQNT SMTLNQPH                                                 18

SEQ ID NO: 47           moltype = AA  length = 18
FEATURE                 Location/Qualifiers
REGION                  1..18
                        note = peptide
source                  1..18
                        mol_type = protein
                        organism = synthetic construct
SEQUENCE: 47
MKPNPSTQNT SMLTNQPH                                                 18

SEQ ID NO: 48           moltype = AA  length = 18
FEATURE                 Location/Qualifiers
```

```
REGION                         1..18
                               note = peptide
source                         1..18
                               mol_type = protein
                               organism = synthetic construct
SEQUENCE: 48
MKPNPATQNT SMTTNQPH                                                          18

SEQ ID NO: 49                  moltype = AA  length = 18
FEATURE                        Location/Qualifiers
REGION                         1..18
                               note = peptide
source                         1..18
                               mol_type = protein
                               organism = synthetic construct
SEQUENCE: 49
MKPNPSTQNT SMTLNYPH                                                          18

SEQ ID NO: 50                  moltype = AA  length = 18
FEATURE                        Location/Qualifiers
REGION                         1..18
                               note = peptide
source                         1..18
                               mol_type = protein
                               organism = synthetic construct
SEQUENCE: 50
MKPNPATQNT SMTTNYPH                                                          18

SEQ ID NO: 51                  moltype = AA  length = 18
FEATURE                        Location/Qualifiers
REGION                         1..18
                               note = peptide
source                         1..18
                               mol_type = protein
                               organism = synthetic construct
SEQUENCE: 51
MKPNPATQNL SMTTNQPH                                                          18

SEQ ID NO: 52                  moltype = AA  length = 18
FEATURE                        Location/Qualifiers
REGION                         1..18
                               note = peptide
source                         1..18
                               mol_type = protein
                               organism = synthetic construct
SEQUENCE: 52
MKPNPSTQNL SMLTNQPH                                                          18

SEQ ID NO: 53                  moltype = AA  length = 18
FEATURE                        Location/Qualifiers
REGION                         1..18
                               note = peptide
source                         1..18
                               mol_type = protein
                               organism = synthetic construct
SEQUENCE: 53
MKPNPSTQNT SMLSNQPH                                                          18

SEQ ID NO: 54                  moltype = AA  length = 18
FEATURE                        Location/Qualifiers
REGION                         1..18
                               note = peptide
source                         1..18
                               mol_type = protein
                               organism = synthetic construct
SEQUENCE: 54
MKPNPATQNT SMLTNQPH                                                          18

SEQ ID NO: 55                  moltype = AA  length = 18
FEATURE                        Location/Qualifiers
REGION                         1..18
                               note = peptide
source                         1..18
                               mol_type = protein
                               organism = synthetic construct
SEQUENCE: 55
MKPNPSTQNL SMTLNQPH                                                          18

SEQ ID NO: 56                  moltype = AA  length = 18
```

-continued

```
FEATURE              Location/Qualifiers
REGION               1..18
                     note = peptide
source               1..18
                     mol_type = protein
                     organism = synthetic construct
SEQUENCE: 56
MKPNPSTQNL SMTTNYPH                                                          18

SEQ ID NO: 57        moltype = AA  length = 18
FEATURE              Location/Qualifiers
REGION               1..18
                     note = peptide
source               1..18
                     mol_type = protein
                     organism = synthetic construct
SEQUENCE: 57
MKPNPATQNT SMTLNQPH                                                          18

SEQ ID NO: 58        moltype = AA  length = 18
FEATURE              Location/Qualifiers
REGION               1..18
                     note = peptide
source               1..18
                     mol_type = protein
                     organism = synthetic construct
SEQUENCE: 58
MKPNPSTQNT SMLTNYPH                                                          18

SEQ ID NO: 59        moltype = AA  length = 18
FEATURE              Location/Qualifiers
REGION               1..18
                     note = peptide
source               1..18
                     mol_type = protein
                     organism = synthetic construct
SEQUENCE: 59
MKPNPSTQNT SMLLNYPH                                                          18

SEQ ID NO: 60        moltype = AA  length = 18
FEATURE              Location/Qualifiers
REGION               1..18
                     note = peptide
source               1..18
                     mol_type = protein
                     organism = synthetic construct
SEQUENCE: 60
MKPNPSTQNL SMTLNYPH                                                          18

SEQ ID NO: 61        moltype = AA  length = 18
FEATURE              Location/Qualifiers
REGION               1..18
                     note = peptide
source               1..18
                     mol_type = protein
                     organism = synthetic construct
SEQUENCE: 61
MKPNPSTQNL SMLTNYPH                                                          18

SEQ ID NO: 62        moltype = AA  length = 18
FEATURE              Location/Qualifiers
REGION               1..18
                     note = peptide
source               1..18
                     mol_type = protein
                     organism = synthetic construct
SEQUENCE: 62
MKPNPSTQNL SMLLNQPH                                                          18

SEQ ID NO: 63        moltype = AA  length = 18
FEATURE              Location/Qualifiers
REGION               1..18
                     note = peptide
source               1..18
                     mol_type = protein
                     organism = synthetic construct
SEQUENCE: 63
MKPNPLTQNT SMTLNYPH                                                          18
```

```
SEQ ID NO: 64              moltype = AA   length = 18
FEATURE                    Location/Qualifiers
REGION                     1..18
                           note = peptide
source                     1..18
                           mol_type = protein
                           organism = synthetic construct
SEQUENCE: 64
MKPNPLTQNT SMLTNYPH                                                        18

SEQ ID NO: 65              moltype = AA   length = 18
FEATURE                    Location/Qualifiers
REGION                     1..18
                           note = peptide
source                     1..18
                           mol_type = protein
                           organism = synthetic construct
SEQUENCE: 65
MKPNPATQNT SMLLNQPH                                                        18

SEQ ID NO: 66              moltype = AA   length = 18
FEATURE                    Location/Qualifiers
REGION                     1..18
                           note = peptide
source                     1..18
                           mol_type = protein
                           organism = synthetic construct
SEQUENCE: 66
MKPNPLTQNL SMTTNYPH                                                        18

SEQ ID NO: 67              moltype = AA   length = 18
FEATURE                    Location/Qualifiers
REGION                     1..18
                           note = peptide
source                     1..18
                           mol_type = protein
                           organism = synthetic construct
SEQUENCE: 67
MKPNPLTQNL SMTLNQPH                                                        18

SEQ ID NO: 68              moltype = AA   length = 18
FEATURE                    Location/Qualifiers
REGION                     1..18
                           note = peptide
source                     1..18
                           mol_type = protein
                           organism = synthetic construct
SEQUENCE: 68
MKPNPATQNL SMLTNQPH                                                        18

SEQ ID NO: 69              moltype = AA   length = 18
FEATURE                    Location/Qualifiers
REGION                     1..18
                           note = peptide
source                     1..18
                           mol_type = protein
                           organism = synthetic construct
SEQUENCE: 69
MKPNPSTQNL SMLLNYPH                                                        18

SEQ ID NO: 70              moltype = AA   length = 18
FEATURE                    Location/Qualifiers
REGION                     1..18
                           note = peptide
source                     1..18
                           mol_type = protein
                           organism = synthetic construct
SEQUENCE: 70
MKPNPATQNT SMLLNYPH                                                        18

SEQ ID NO: 71              moltype = AA   length = 18
FEATURE                    Location/Qualifiers
REGION                     1..18
                           note = peptide
source                     1..18
                           mol_type = protein
                           organism = synthetic construct
SEQUENCE: 71
MKPNPATQNL SMTLNYPH                                                        18
```

```
SEQ ID NO: 72            moltype = AA  length = 18
FEATURE                  Location/Qualifiers
REGION                   1..18
                         note = peptide
source                   1..18
                         mol_type = protein
                         organism = synthetic construct
SEQUENCE: 72
MKPNPATQNL SMLTNYPH                                                       18

SEQ ID NO: 73            moltype = AA  length = 18
FEATURE                  Location/Qualifiers
REGION                   1..18
                         note = peptide
source                   1..18
                         mol_type = protein
                         organism = synthetic construct
SEQUENCE: 73
MKPNPATQNL SMLLNQPH                                                       18

SEQ ID NO: 74            moltype = AA  length = 18
FEATURE                  Location/Qualifiers
REGION                   1..18
                         note = peptide
source                   1..18
                         mol_type = protein
                         organism = synthetic construct
SEQUENCE: 74
AKPNPATANL SMLLNYPA                                                       18

SEQ ID NO: 75            moltype = AA  length = 18
FEATURE                  Location/Qualifiers
REGION                   1..18
                         note = peptide
source                   1..18
                         mol_type = protein
                         organism = synthetic construct
SEQUENCE: 75
MAPNPATQNA SMLLNYAH                                                       18

SEQ ID NO: 76            moltype = AA  length = 18
FEATURE                  Location/Qualifiers
REGION                   1..18
                         note = peptide
source                   1..18
                         mol_type = protein
                         organism = synthetic construct
SEQUENCE: 76
MKPAPATANL SMLLNYAH                                                       18

SEQ ID NO: 77            moltype = AA  length = 18
FEATURE                  Location/Qualifiers
REGION                   1..18
                         note = peptide
source                   1..18
                         mol_type = protein
                         organism = synthetic construct
SEQUENCE: 77
MKPAPATQAL SMLLAYPH                                                       18

SEQ ID NO: 78            moltype = AA  length = 18
FEATURE                  Location/Qualifiers
REGION                   1..18
                         note = peptide
source                   1..18
                         mol_type = protein
                         organism = synthetic construct
SEQUENCE: 78
MKPNAATQAL SMLANYPH                                                       18

SEQ ID NO: 79            moltype = AA  length = 18
FEATURE                  Location/Qualifiers
REGION                   1..18
                         note = peptide
source                   1..18
                         mol_type = protein
                         organism = synthetic construct
SEQUENCE: 79
```

```
MAPNPAAQNL SALLNYPH                                                                 18

SEQ ID NO: 80           moltype = AA  length = 18
FEATURE                 Location/Qualifiers
REGION                  1..18
                        note = peptide
source                  1..18
                        mol_type = protein
                        organism = synthetic construct
SEQUENCE: 80
MKPNPATQNL SMALAYAH                                                                 18

SEQ ID NO: 81           moltype = AA  length = 18
FEATURE                 Location/Qualifiers
REGION                  1..18
                        note = peptide
source                  1..18
                        mol_type = protein
                        organism = synthetic construct
SEQUENCE: 81
AKPAPAAQNL SMLLNYPH                                                                 18

SEQ ID NO: 82           moltype = AA  length = 18
FEATURE                 Location/Qualifiers
REGION                  1..18
                        note = peptide
source                  1..18
                        mol_type = protein
                        organism = synthetic construct
SEQUENCE: 82
MKPNPATQNL SMALAYPA                                                                 18

SEQ ID NO: 83           moltype = AA  length = 18
FEATURE                 Location/Qualifiers
REGION                  1..18
                        note = peptide
source                  1..18
                        mol_type = protein
                        organism = synthetic construct
SEQUENCE: 83
MKPNAATANL AMLLNYPH                                                                 18

SEQ ID NO: 84           moltype = AA  length = 18
FEATURE                 Location/Qualifiers
REGION                  1..18
                        note = peptide
source                  1..18
                        mol_type = protein
                        organism = synthetic construct
SEQUENCE: 84
MKPNPATQAL SMALNAPH                                                                 18

SEQ ID NO: 85           moltype = AA  length = 18
FEATURE                 Location/Qualifiers
REGION                  1..18
                        note = peptide
source                  1..18
                        mol_type = protein
                        organism = synthetic construct
SEQUENCE: 85
MAPNAATQNA SMLLNYPH                                                                 18

SEQ ID NO: 86           moltype = AA  length = 18
FEATURE                 Location/Qualifiers
REGION                  1..18
                        note = peptide
source                  1..18
                        mol_type = protein
                        organism = synthetic construct
SEQUENCE: 86
AKANPATQNL SMLLNYPH                                                                 18

SEQ ID NO: 87           moltype = AA  length = 18
FEATURE                 Location/Qualifiers
REGION                  1..18
                        note = peptide
source                  1..18
                        mol_type = protein
                        organism = synthetic construct
```

```
SEQUENCE: 87
MAPAPATQNL SMLLNYPH                                                   18

SEQ ID NO: 88           moltype = AA  length = 18
FEATURE                 Location/Qualifiers
REGION                  1..18
                        note = peptide
source                  1..18
                        mol_type = protein
                        organism = synthetic construct
SEQUENCE: 88
MKPAPAAQNL SMLLNYPH                                                   18

SEQ ID NO: 89           moltype = AA  length = 18
FEATURE                 Location/Qualifiers
REGION                  1..18
                        note = peptide
source                  1..18
                        mol_type = protein
                        organism = synthetic construct
SEQUENCE: 89
MKPNAAAQNL SMLLNYPH                                                   18

SEQ ID NO: 90           moltype = AA  length = 18
FEATURE                 Location/Qualifiers
REGION                  1..18
                        note = peptide
source                  1..18
                        mol_type = protein
                        organism = synthetic construct
SEQUENCE: 90
MKPNPATANA SMLLNYPH                                                   18

SEQ ID NO: 91           moltype = AA  length = 18
FEATURE                 Location/Qualifiers
REGION                  1..18
                        note = peptide
source                  1..18
                        mol_type = protein
                        organism = synthetic construct
SEQUENCE: 91
MKPNPATQAL AMLLNYPH                                                   18

SEQ ID NO: 92           moltype = AA  length = 18
FEATURE                 Location/Qualifiers
REGION                  1..18
                        note = peptide
source                  1..18
                        mol_type = protein
                        organism = synthetic construct
SEQUENCE: 92
MKPNPATQNA SALLNYPH                                                   18

SEQ ID NO: 93           moltype = AA  length = 18
FEATURE                 Location/Qualifiers
REGION                  1..18
                        note = peptide
source                  1..18
                        mol_type = protein
                        organism = synthetic construct
SEQUENCE: 93
MKPNPATQNL AMALNYPH                                                   18

SEQ ID NO: 94           moltype = AA  length = 18
FEATURE                 Location/Qualifiers
REGION                  1..18
                        note = peptide
source                  1..18
                        mol_type = protein
                        organism = synthetic construct
SEQUENCE: 94
MKPNPATQNL SALANYPH                                                   18

SEQ ID NO: 95           moltype = AA  length = 18
FEATURE                 Location/Qualifiers
REGION                  1..18
                        note = peptide
source                  1..18
                        mol_type = protein
```

```
SEQUENCE: 95
MKPNPATQNL SMALAYPH                                              18

SEQ ID NO: 96           moltype = AA  length = 18
FEATURE                 Location/Qualifiers
REGION                  1..18
                        note = peptide
source                  1..18
                        mol_type = protein
                        organism = synthetic construct
SEQUENCE: 96
MKPNPATQNL SMLANAPH                                              18

SEQ ID NO: 97           moltype = AA  length = 18
FEATURE                 Location/Qualifiers
source                  1..18
                        mol_type = protein
                        organism = Homo sapiens
SEQUENCE: 97
MKPNPATQNL SMLLNYPH                                              18

SEQ ID NO: 98           moltype = DNA  length = 57
FEATURE                 Location/Qualifiers
source                  1..57
                        mol_type = genomic DNA
                        organism = Homo sapiens
SEQUENCE: 98
attaaaccaa acccagctac gcaaaatctt agcatactcc tcaattaccc acatagg    57
```